US008859240B2

(12) United States Patent
Tangy et al.

(10) Patent No.: US 8,859,240 B2
(45) Date of Patent: Oct. 14, 2014

(54) DENGUE AND WEST NILE VIRUSES PROTEINS AND GENES CODING THE FOREGOING, AND THEIR USE IN VACCINAL, THERAPEUTIC AND DIAGNOSTIC APPLICATIONS

(75) Inventors: Frédéric Tangy, les Lilas (FR); Philippe Despres, Garenne-Colombes (FR); Chantal Combredet, Paris (FR); Marie Pascale Frenkiel, Levallois (FR)

(73) Assignees: Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 1535 days.

(21) Appl. No.: 12/476,304

(22) Filed: Jun. 2, 2009

(65) Prior Publication Data

US 2013/0089558 A1 Apr. 11, 2013

Related U.S. Application Data

(63) Continuation of application No. 11/210,960, which is a continuation of application No. PCT/IB2004/001027, filed on Feb. 26, 2004, now Pat. No. 7,556,812.

(30) Foreign Application Priority Data

Feb. 26, 2003 (CA) .................................... 2,420,092
Jun. 20, 2003 (CA) .................................... 2,432,738

(51) Int. Cl.

| | |
|---|---|
| *A61K 38/00* | (2006.01) |
| *A61K 39/12* | (2006.01) |
| *C07K 14/18* | (2006.01) |
| *C12N 15/86* | (2006.01) |
| *C12Q 1/70* | (2006.01) |
| *C07K 14/005* | (2006.01) |
| *A61K 39/00* | (2006.01) |

(52) U.S. Cl.

CPC ....... *A61K 39/12* (2013.01); *C12N 2770/24122* (2013.01); *C07K 14/1825* (2013.01); *A61K 2039/53* (2013.01); *C12N 15/86* (2013.01); *C12Q 1/701* (2013.01); *A61K 39/00* (2013.01); *C07K 14/005* (2013.01); *C12N 2760/18443* (2013.01); *A61K 38/00* (2013.01); *A61K 2039/5256* (2013.01)

USPC ...... 435/91.33; 435/5; 435/320.1; 435/91.32; 435/456; 435/236; 435/235.1; 435/252.33; 435/254.2; 435/254.21; 435/254.23; 435/325; 435/348; 435/419; 424/139.1; 424/186.1; 530/350; 530/387.9; 530/395

(58) Field of Classification Search

CPC ............. C07K 14/1825; C07K 14/005; A61K 2039/53; A61K 2039/5256; A61K 39/00; A61K 39/12; A61K 38/00; C12N 15/86; C12N 2760/18443; C12N 2770/24122; C12Q 1/701

See application file for complete search history.

(56) References Cited

U.S. PATENT DOCUMENTS

| | | | | |
|---|---|---|---|---|
| 5,654,136 | A | 8/1997 | Sasaki | |
| 6,146,642 | A | 11/2000 | Garcia-Sastre | |
| 7,402,429 | B1 | 7/2008 | Billeter | |
| 7,556,812 | B2 | 7/2009 | Tangy et al. | |
| 7,851,214 | B2 | 12/2010 | Billeter | |
| 7,993,924 | B2 | 8/2011 | Billeter | |
| 8,158,416 | B2 | 4/2012 | Billeter | |
| 8,586,364 | B2 | 11/2013 | Tangy et al. | |
| 2002/0155581 | A1* | 10/2002 | Murphy et al. | 435/235.1 |
| 2005/0186563 | A1 | 8/2005 | Hoffmann | |
| 2005/0227224 | A1* | 10/2005 | Tangy et al. | 435/5 |
| 2006/0013826 | A1* | 1/2006 | Tangy et al. | 424/199.1 |
| 2006/0073164 | A1* | 4/2006 | Tangy et al. | 424/204.1 |
| 2007/0275002 | A1* | 11/2007 | Van Der Werf et al. | 424/186.1 |
| 2007/0280961 | A1 | 12/2007 | Billeter | |
| 2008/0124803 | A1 | 5/2008 | Billeter | |
| 2010/0226924 | A1* | 9/2010 | Tangy et al. | 424/139.1 |

(Continued)

FOREIGN PATENT DOCUMENTS

| | | | |
|---|---|---|---|
| EP | 0440219 | A1 * | 1/1991 |
| EP | 1375670 | A1 * | 1/2004 |

(Continued)

OTHER PUBLICATIONS

Delenda C, Staropoli I, Frenkiel MP, Cabanié L, Deubel V. Analysis of C-terminally truncated dengue 2 and dengue 3 virus envelope glycoproteins: processing in insect cells and immunogenic properties in mice. J Gen Virol. Jul. 1994;75 ( Pt 7):1569-78.*

(Continued)

*Primary Examiner* — Benjamin P Blumel
*Assistant Examiner* — Rachel Gill
(74) *Attorney, Agent, or Firm* — Law Office of Salvatore Arrigo and Scott Lee, LLP

(57) ABSTRACT

The present invention relates to the development of viral vectors expressing different immunogens from the West Nile Encephalitis Virus (WNV) or the Dengue virus which are able to induce protective humoral and cellular immune responses against WNV or Dengue virus infections. More specifically, the present invention relates to three (3) antigens from WNV (the secreted envelope glycoprotein (E), the heterodimer glycoproteins (pre-M-E) and the NSI protein) and from Dengue virus (the secreted envelope glycoprotein (e), the heterodimer glycoproteins (pre-m-e) and the nsl protein) and their use in vaccinal, therapeutic and diagnostic applications.

14 Claims, 7 Drawing Sheets

(56) References Cited

U.S. PATENT DOCUMENTS

| | | | |
|---|---|---|---|
| 2010/0278872 A1* | 11/2010 | Gauvrit et al. | 424/277.1 |
| 2011/0129493 A1 | 6/2011 | Mendiretta | |
| 2011/0236468 A1* | 9/2011 | Lorin et al. | 424/450 |
| 2011/0311581 A1* | 12/2011 | Miled et al. | 424/204.1 |
| 2012/0082693 A1* | 4/2012 | Van Der Werf et al. | 424/186.1 |
| 2012/0121538 A1 | 5/2012 | Glueck | |
| 2012/0201825 A1* | 8/2012 | Tangy et al. | 424/139.1 |
| 2013/0052218 A1* | 2/2013 | Tangy et al. | 424/199.1 |
| 2013/0296541 A1 | 11/2013 | Tangy | |

FOREIGN PATENT DOCUMENTS

| | | | |
|---|---|---|---|
| EP | 1454988 A1 * | 9/2004 | |
| WO | 90/01946 | 3/1990 | |
| WO | 9706270 | 2/1997 | |
| WO | 98/13500 | 4/1998 | |
| WO | 9813501 | 4/1998 | |
| WO | WO 98/13501 A1 * | 4/1998 | |
| WO | 9837911 | 9/1998 | |
| WO | 0109309 A2 | 2/2001 | |
| WO | 02/072036 A2 | 9/2002 | |
| WO | WO 02081754 A1 * | 10/2002 | |
| WO | 2004/001051 A3 | 12/2003 | |
| WO | 2004000876 A1 | 12/2003 | |

OTHER PUBLICATIONS

Ocazionez Jimenez R, Lopes da Fonseca BA. Recombinant plasmid expressing a truncated dengue-2 virus E protein without co-expression of prM protein induces partial protection in mice. Vaccine. Nov. 8, 2000;19(6):648-54.*

Singh M, Cattaneo R, Billeter MA. A recombinant measles virus expressing hepatitis B virus surface antigen induces humoral immune responses in genetically modified mice. J Virol. Jun. 1999;73(6):4823-8.*

Papa A, Karabaxoglou D, Kansouzidou A. Acute West Nile virus neuroinvasive infections: cross-reactivity with dengue virus and tick-borne encephalitis virus. J Med Virol. Oct. 2011;83(10):1861-5.*

Crill WD, Trainor NB, Chang GJ. A detailed mutagenesis study of flavivirus cross-reactive epitopes using West Nile virus-like particles. J Gen Virol. Apr. 2007;88(Pt 4):1169-74.*

Petersen LR, Brault AC, Nasci RS. West Nile virus: review of the literature. JAMA. Jul. 17, 2013;310(3):308-15.*

Back AT, Lundkvist A. Dengue viruses—an overview. Infect Ecol Epidemiol. Aug. 30, 2013;3.*

Heinz FX, Stiasny K. Flaviviruses and flavivirus vaccines. Vaccine. Jun. 19, 2012;30(29):4301-6.*

Van Binnendijk RS et al. Protective immunity in macaques vaccinated with live attenuated, recombinant and subunit measles vaccines in the presence of passively acquired antibodies. Journal of Infectious Diseases, 1997, 175: 524-532.*

Men RH, Bray M, Lai CJ. Carboxy-terminally truncated dengue virus envelope glycoproteins expressed on the cell surface and secreted extracellularly exhibit increased immunogenicity in mice. J Virol. Mar. 1991;65(3):1400-7.*

Takeuchi K, Takeda M, Miyajima N, Kobune F, Tanabayashi K, Tashiro M. Recombinant wild-type and edmonston strain measles viruses bearing heterologous H proteins: role of H protein in cell fusion and host cell specificity. J Virol. May 2002;76(10):4891-900.*

Hashimoto K, Ono N, Tatsuo H, Minagawa H, Takeda M, Takeuchi K, Yanagi Y. SLAM (CD150)-independent measles virus entry as revealed by recombinant virus expressing green fluorescent protein. J Virol. Jul. 2002;76(13):6743-9.*

Nagai Y. Paramyxovirus replication and pathogenesis. Reverse genetics transforms understanding. Rev Med Virol. Apr.-Jun. 1999;9(2):83-99.*

Fisher LE. Arch Virol.1983;77(I):51-60.*

Roberts A, Rose JK. Recovery of negative-strand RNA viruses from plasmid DNAs: a positive approach revitalizes a negative field. Virology. Jul. 20, 1998;247(1):1-6.*

Radecke F, Billeter MA. The nonstructural C protein is not essential for multiplication of Edmonston B strain measles virus in cultured cells. Virology. Mar. 1, 1996;217(1):418-21.*

Fukuda A, Sugiura A. Temperature-dependent growth restriction in measles vaccine strains. Jpn J Med Sci Biol. Dec. 1983;36(6):331-5.*

Rota JS, et. al. Virus Res. Mar. 1994;31(3):317-30.*

Phuong LK, Allen C, Peng KW, Giannini C, Greiner S, TenEyck CJ, Mishra PK, Macura SI, Russell SJ, Galanis EC. Use of a vaccine strain of measles virus genetically engineered to produce carcinoembryonic antigen as a novel therapeutic agent against glioblastoma multiforme. Cancer Res. May 15, 2003;63(10):2462-9.*

Takeuchi K, Takeda M, Miyajima N. Toward understanding the pathogenicity of wild-type measles virus by reverse genetics. Jpn J Infect Dis. Oct. 2002;55(5):143-9.*

Courageot et al., alpha-Glucosidase Inhibitors Reduce Dengue Virus Production by Affecting the Initial Steps of Virion Morphogenesis in the Endoplasmic Reticulum, Journal of Virology, vol. 74, No. 1, pp. 564-572 (2000).

Lanciotti et al., Origin of the West Nile Virus Responsible for an Outbreak of Encephalitis in the Northeastern United States, Science, vol. 286, No. 5448, pp. 2334-2337 (1999).

Wang at al., Immunization of Mice Against West Nile Virus with Recombinant Envelope Protein, Journal of Immunology, vol. 167, pp. 5273-5277 (2001).

Davis et al., West Nile Virus Recombinant DNA Vaccine Protects Mouse and Horse From Virus Challenge and Expresses in Vitro a Noninfectious Recombinant Antigen That Can Be Used in Enzyme-Linked Immunosorbent Assays, Journal of Virology, vol. 75, No. 9, pp. 4040-4047 (2001).

Wang et al., Recombinant Measles Viruses Expressing Heterologous Antigens of Mumps and Simian Immunodeficiency Viruses, Vaccine, vol. 19, No. 17-19, pp. 2329-2336 (2001).

Combredet et al., A Molecularly Cloned Schwarz Strain of Measles Virus Vaccine Induces Strong Immune Responses in Macaques and Transgenic Mice, Journal of Virology, vol. 77, No. 21, pp. 11546-11554 (2003).

Despres et al., Differences Between Cell Membrane Fusion Activities of Two Dengue Type-1 Isolates Reflect Modifications of Viral Structure, Virology, vol. 196, No. 1, pp. 209-219 (1993).

Pletnev et al., West Nile Virus/Dengue Type 4 Virus Chimeras That Are Reduced in Neurovirulence and Peripheral Virulence Without Loss of Immunogenicity or Protective Efficacy, Proceedings of the National Academy of Sciences, USA, vol. 99, No. 5, pp. 3036-3041 (2002).

Duarte Dos Santos, at al., Determinants in the Envelope E Protein and Viral RNA Helicase NS3 That Influence the Induction of Apoptosis in Response to Infection With Dengue Type 1 Virus, Virology, vol. 274, No. 2, pp. 292-308 (2000).

Duarte Dos Santos, et al., Denque Virus Type 1 Strain FGA189, Complete Genome, Abstract retrieved from EBI, Database accession No. AF226687, 5 pages, (2001).

Fonseca et al., Recombinant Vaccinia Viruses Co-Expressing Dengue-1 Glycdproteins prM and E Induce Neutralizing Antibodies in Mice, Vaccine, vol. 12, No. 3, pp. 279-285 (1994).

Basselaar et al., Antigenic Analysis of West Nile Virus Strains Using Monoclonal Antibodies, Archives of Virology, vol. 99, No. 1-2, pp. 75-88 (1988).

Mercy et al., A New Series of TRPE Vectors That Enable High Expression of Nonfusion Proteins in Bacteria, Protein Expression and Purification, vol. 3, No. 1, pp. 57-64 (1992) (Abstract only cited).

Genbank locus AAF20205, May 8, 2000.

Genbank locus AAL87234, May 21, 2002.

International Search Report for PCT/IB2004/001027.

International Preliminary Report on Patentability for PCTIIE32004/001027.

Eckels et al., Formalin-Inactivated Whole Virus and Recombinant Subunit Flavivirus Vaccines, Advances in Virus Research, vol. 61, pp. 395-418 (2003).

Combredet, Chantal, et al., "A Molecularly Cloned Schwarz Strain of Measles Virus Vaccine Induces Strong Immune Responses in Macaques and Transgenic Mice," Journal of Virology, vol. 77, No. 21, pp. 11546-11554 (2003).

(56) References Cited

OTHER PUBLICATIONS

Dilraj, Athmanundh, et al., "Response to different measles vaccine strains given by aerosol and subcutaneous routes to schoolchildren: a randomised trial," The Lancet, vol. 355, pp. 798-2000 (2000).

Lorin, Clarisse, et al., "A Single Injection of Recombinant Measles Virus Vaccines Expressing Human Immunodeficiency Virus (HIV) Type 1 Clade B Envelope Glycoproteins Induces Neutralizing Antibodies and Cellular Immune Responses to HIV," Journal of Virology, vol. 78, No. 1, pp. 146-157 (2004).

Monath, Thomas P., "Prospects for Development of a Vaccine against the West Nile Virus," vol. 951, pp. 1-12 (2001).

Monath, Thomas P., "West Nile Virus Vaccine," Current Drug Targets—Infectious Disorders, vol. 1, pp. 37-50 (2001).

Redecke, Frank, et al., "Rescue of measles viruses from cloned DNA," The EMBY Journal, vol. 14, No. 23, pp. 5773-5784 (1995).

Redecke, Frank, et al., "Reverse Genetics Meets the Nonsegmented Negative-Strand RNA Viruses," Reviews in Medical Virology, vol. 7, pp. 49-63 (1997).

Singh, Mahender, et al., "A Recombinant Measles Virus Expressing Hepatitis B Virus Surface Antigen Induces Humoral Immune Responses in Genetically Modified Mice," Journal of Virology, vol. 73, No. 6, pp. 4823-4828 (1999).

Spielhofer, Pius, et al., "Chimeric Measles Viruses with a Foreign Envelope," Journal of Virology, vol. 72, No. 3, pp. 2150-2159 (1998).

Wang, Tian, et al., "Immunization of Mice Against West Nile Virus with Recombinant Envelope Protein," The Journal of Immunology, vol. 167, pp. 5273-5277 (2001).

Borges, Maria Beatriz Junqueira, et al., "Biological Characterization of Clones Derived from the Edmonston Strain of Measles Virus in Comparison with Schwarz and CAM-71 Vaccine Strains," Mem. Inst. Oswaldo Cruz, Rio de Janeiro, vol. 91, No. 4, pp. 507-514 (1996).

Parks, Christopher L., et al., "Enhanced Measles Virus cDNA Rescue and Gene Expression after Heat Shock," Journal of Virology, vol. 73, No. 5, pp. 3560-3566 (1999).

Parks, Christopher L., et al., "Comparison of Predicted Amino Acid Sequences of Measles Virus Strains in the Edmonston Vaccine Lineage," Journal of Virology, vol. 75, No. 2, pp. 910-920 (2001).
Takada, Makoto, et al., "Recovery of Pathogenic Measles Virus from Cloned cDNA," Journal of Virology, vol. 74, No. 14, pp. 6643-6647 (2000).
Arroyo, Juan, et al., "Yellow fever vector live-virus vaccines: West Nile virus vaccine development," TRENDS in Molecular Medicine, vol. 7, No. 8, pp. 350-354 (2001).
Colombage, G., et al., "DNA-Based and Alphavirus-Vectored Immunisation with PrM and E Proteins Elicits Long-Lived and Protective Immunity against the Flavivirus, Murray Valley Encephalitis Virus," Virology, vol. 250, pp. 151-163 (1998).
Despres, Phillippe, et al., "Live Measles Vaccine Expressing the Secreted Form of the West Nile Virus Envelope Glycoprotein Protects against West Nile Virus Encephalitis," Journal of Infectious Diseases, vol. 191, pp. 207-214 (2005).
Malkinson, Mertyn, et al., "Introduction of West Nile virus in the Middle East by Migrating White Storks," Emerging Infectious Diseases, vol. 8, No. 4, pp. 392-397 (2002).
Muster, Thomas, et al., "A Conserved Neutralizing Epitope on gp41 of Human Immunodeficiency Virus Type 1," Journal of Virology, vol. 67, No. 11, pp. 6642-6647 (1993).
Sanders, Rogier W., et al., "Variable-Loop-Deleted Variants of the Human Immunodeficiency Virus Type 1 Envelope Glycoprotein Can Be Stabilized by an Intermolecular Disulfide Bond Between the gp120 and gp41 Subunits," Journal of Virology, vol. 74, No. 11, pp. 5091-5100 (2000).
Schlereth, Bernd, et al., "Successful Vaccine-Induced Seroconversion by Single-Dose Immunization in the Presence of Measles Virus-Specific Maternal Antibodies," Journal of Virology, vol. 74, No. 10, pp. 4652-4657 (2000).
Tangy, F., et al., "Measles Vaccine as a Potential Vector for AIDS Vaccination," AIDS Vaccine Conference, 2001.
Genbank locus AF266286.1, Measles virus strain Edmonston (AIK-C vaccine), complete genome, Jan. 25, 2001.
Genbank locus AF266287.1, Measles virus strain Edmonston (Moraten vaccine), complete genome, Jan. 25, 2001.
Genbank locus AF266289.1, Measles virus strain Edmonston (Rubeovax vaccine), complete genome, Jan. 25, 2001.
Genbank locus AF266290.1, Measles virus strain Edmonston (Zagreb vaccine), complete genome, Jan. 25, 2001.
Genbank locus AF266291.1, Measles virus strain Edmonston (Schwarz vaccine), complete genome, Jan. 25, 2001.
Barnett, S. W., et al., "The Ability of an Oligomeric Human I mmunodeficiency Virus Type 1 (HIV-1) Envelope Antigen to Elicit Neutralizing Antibodies against Primary HIV-1 Isolates is Improved following Partial Deletion of the Second Hypervariable Region," J. Virol., vol. 75, No. 12, pp. 5526-5540 (2001).
Collman, R., et al., "An infectious molecular clone of an unusual macrophage-tropic and highly cytopathic strain of human immunodeficiency virus type 1," J. Virol., vol. 66, No. 12, pp. 7517-7521 (1992).
Domingo, Esteban, et al., "Symposium: Newly Emerging Viral Diseases: What Role for Nutrition?", J. Nutr., vol. 127, pp. 958S-961S (1997).
Duprex, W. Paul, et al., Observation of Measles Virus Cell-to-Cell Spread in Astrocytoma Cells by Using a Green Fluorescent Protein-Expressing Recombinant Virus, Journal of Virology, vol. 73, No. 11, pp. 9568-9575 (1999).
Escoffier, Carine, et al., "Infection of Chicken Embryonic Fibroblasts by Measles Virus: Adaptation at the Virus Entry Level," Journal of Virology, vol. 73, No. 6, pp. 5220-5224 (1999).
Horikami, Sandra M. et al., Synthesis of Leader RNA and Editing of the P mRNA during Transcription by Purified Measles Virus, Journal of Virology, vol. 65, No. 10, pp. 5342-5347 (1991).
Libman, Michael D., et al., "No evidence for short or long term morbidity after increased titer measles vaccination in Sudan," The Pediatric Infectious Disease Journal, vol. 21, No. 2, pp. 112-119 (2002).
Mrkic, Branka, et al., "Measles Virus Spread and Pathogenesis in Genetically Modified Mice," Journal of Virology, vol. 72, No. 9, pp. 7420-7427 (1998).
Naniche, Denise, et al., "Human Membrane Cofactor Protein (CD46) Acts as a Cellular Receptor for Measles Virus," Journal of Virology, vol. 67, No. 10 (1993).
Ndumbe, Peter M., et al., "Comparison of Edmonston-Zagreb, Connaught and Schwarz measles vaccines in Cameroonian infants aged 3-8 months," Vaccine, vol. 13, No. 3, pp. 276-2809 (1995).
Palese, Peter, et al., "Negative-strand RNA viruses: Genetic engineering and applications," PNAS, USA, vol. 93, pp. 11354-11358 (1996).
Parks, Christopher L., et al., "Analysis of the Noncoding Regions of Measles Virus Strains in the Edmonston Vaccine Lineage," Journal of Virology, vol. 75, No. 2, pp. 921-933 (2001).
Pugachev, Konstantin V., et al., "Improvement of the Specific Infectivity of the Rubella Virus (RUB) Infectious Clone: Determinants of Cytopathogenicity Induced by RUB Map to the Nonstructural Proteins," Journal of Virology, vol. 71, No. 1, pp. 562-568 (1997).
Reimann, K. A., et al., "A chimeric simian/human immunodeficiency virus expressing a primary patient human immunodeficiency virus type 1 isolate env causes AIDS-like disease after in vivo passage in rhesus monkeys," Journal of Virology, vol. 70, No. 10, pp. 6922-6928 (1996).
Rice, Charles M., et al., Production of Infectious RNA Transcripts from Sindbis Virus cDNA Clones: Mapping of Lethal Mutations, Rescue of a Temperature-Sensitive Marker, and in Vitro Mutagenesis to Generate Defined Mutants, Journal of Virology, vol. 61, No. 12 (1987).
Rose, Nina F., et al., An Effective AIDS Vaccine Based on Live Attenuated Vesicular Stomatitis Virus Recombinants, Cell, vol. 106, pp. 539-549 (2001).
Ruggli, Nicolas, et al., Nucleotide Sequence of Classical Swine Fever Virus Strain Alfort/187 and Transription of Infectious RNA from Stably Cloned Full-Length cDNA, Journal of Virology, vol. 70, No. 6, pp. 3478-3487 (1996).
SCORE results in "nr" datrabase for Seq ID No. 82 (pTM-MVSchw), nucleotide 83-15977; 29-16202; 29-15977; 26-16202; 9-16202 (2007).

(56) References Cited

OTHER PUBLICATIONS

Singh, Mahender, et al., "A recombinant measles virus expressing biologically active human interleukin-12," Journal of General Virology, vol. 80, pp. 101-106 (1999).
Takeuchi, Kaoru, et al., "Toward Understanding the Pathogenicity of Wild-Type Measles Virus by Reverse Genetics," Jpn. J. Infect. Dis., vol. 55, pp. 143-149 (2002).
Tangy, F., et al., Molecular cloning of the complete genome of strain GDVII of Theiler's virus and production of infectious transcripts, Journal of Virology, vol. 63, No. 3, pp. 1101-1106 (1989).
Van Binnendijk, R. S., et al., "Monkeys in Measles Research," Curr. Top. Microbiol. Immuno., vol. 191, pp. 135-148 (1995).
Van Binnendijk, R. S., et al., "Viral Replication and Development of Specific Immunity in Macaques after Infection with Different Measles Virus Strains," vol. 170, pp. 443-448 (1994).
Walsh, Edmund., et al., "Development of a genetically marked recombinant rinderpest vaccine expressing green fluorescent protein," Journal of General Virology, vol. 81, pp. 709-718 (2000).
Wang, Chin-Yen, et al., "Construction of Rubella Virus Genome-Length cDNA Clones and Synthesis of Infectious RNA Transcripts," Journal of Virology, vol. 68, No. 6, pp. 3550-3557 (1994).
Bernstein, Theodore, et al., "Persistent Infection of BSC-1 Cells by Defective Measles Virus Derived From Subacute Sclerosing Panencephalitis," Infect. Immun., vol. 10, No. 6, pp. 1378-1382 (1974).
Hammond, Anthea L., et al., "Single-Chain Antibody Displayed on a Recombinant Measles Virus Confers Entry through the Tumor-Associated Carcinoembryonic Antigen," Journal of Virology, vol. 75, No. 5, pp. 2087-2096 (2001).
Lund, G. A., et al., "The Molecular Length of Measles Virus RNA and the Structural Organization of Measles Nucleocapsids," J. Gen. Virol., vol. 65, pp. 1535-1542 (1984).
Plemper, Richard K, "Measles Virus Envelope Glycoproteins Hetero-Oligomerize in the Endoplasmic Reticulum," The Journal of Biological Chemistry, vol. 276, No. 47, pp. 44239-44246 (2001).
Schneider, Henriette, et al., "Rescue of measles virus using a replication-deficient vaccinia-T7 vector," Journal of Virological Methods, vol. 64, pp. 57-64 (1997).
Syrucek, L., et al., Comparative Trial of Live Measles Vaccines in Czechoslovakia, Bull. Org. mond. Sante, vol. 32, pp. 779-789 (1965).
Betakova, T., et al., "Overview of measles and mumps vaccine: origin, present, and future of vaccine production," Acta Virologica, vol. 57, pp. 91-96 (2013).
Bitnum, Ari, et al., "Measles Inclusion-Body Encephalitis Caused by the Vaccine Strain of Measles Virus," Clinical Infectious Diseases, vol. 29, pp. 855-861 (1999).
Buchanan, Renee, et al., "Measles Virus and Associated Central Nervous System Sequelae," Semiars in Pediatric Neurology, vol. 19, pp. 107-114 2012).
Centers for Desease Prevention and Control (CDC), Measles: Pink Sheet May 2012.
Collins, Peter L., "Letter to the Editor; What Are the Risks—Hypothetical and Observed—of Recombination Involving Live Vaccines and Vaccine Vectors Based on Nonsegmented Negative-Strain RNA Viruses?", Journal of Virology, vol. 82, No. 19, pp. 9805-9806 (2008).
Johnson, Jeffrey A., et al., "Characterization of Endogenous Avian Leukosis Viruses in Chicken Embryonic Fibroblast Substrates Used in Production of Measles and Mumps Vaccines," Journal of Virology, vol. 75, No. 8, pp. 3605-3612 (2001).
Mortimer, E. A., et al., "Communicable Diseases," p. 245, Pless, I. B., Ed., The Epidemiology of Childhood Disorders, Oxford University Press, 1994.
Plumet, Sebastien, et al., "Dynamics of Viral RNA Synthesis During Measles Virus Infection," Journal of Virology, vol. 79, No. 11, pp. 6900-6908 (2005).
Stokes, J. et al., "Efficacy of Live, Attenuated Measles-Virus Vaccine Given With Human Immune Globulin," The New England Journal of Medicine, vol. 265, No. 11, pp. 507-513 (1961).
Takata, C.S., et al., "Susceptibiligy of Vero cell line to vaccine strains of the measled virus," Rev. Saude Publica., vol. 28, No. 3, pp. 209-212 (1994) (Abstract).
Vesikari, T., et al., "Clinical trial of a new trivalent measles-mumps-rubella vaccine in young children," vol. 138, No. 9, pp. 843-847 (1984) (Abstract).
Yamanouchi, Kazuya, et al., "Giant Cell Formation in Lymphoid Tissues of Monkeys Inoculated With Various Strains of Measles Virus," Japan J. Med. Sci. Biol., vol. 23, pp. 1310-1145 (1970).
Zhang, Xiaomeng, et al., "Determination of Spontaneous Mutation Frequencies in Measles Virus under Nonselective Conditions," J. Virol., vol. 87, No. 5, pp. 2686-2692 (2013).
Ballart, Isidro, et al., "Infectious measles virus from cloned cDNA," EMBO J., vol. 9, No. 2, pp. 379-384 (1990); Retraction in Ballart, Isidro, et al., EMBO J., vol. 10, No. 11, p. 3558 (1991). Retracted.
Kolakofsky, Daniel, et al., "Paramyxovirus RNA Synthesis and the Requirement for Hexamer Genome Length: the Rule of Six Revisited," J. Virol., vol. 72, No. 2, pp. 891-899 (1998).

\* cited by examiner

Figure 1 atgagagttgtgtttgtcgtgctattgcttttggtggccccagcttacagcttcaactgccttggaatgagcaacagagactt
cttggaaggagtgtctggagcaacatgggtggatttggttctcgaaggcgacagctgcgtgactatcatgtctaaggac
aagcctaccatcgatgtgaagatgatgaatatggaggcggtcaacctggcagaggtccgcagttattgctatttggcta
ccgtcagcgatctctccaccaaagctgcgtgcccgaccatgggagaagctcacaatgacaaacgtgctgacccagc
ttttgtgtgcagacaaggagtggtggacaggggctggggcaacggctgcggattatttggcaaaggaagcattgaca
catgcgccaaatttgcctgctctaccaaggcaataggaagaaccatcttgaaagagaatatcaagtacgaagtggcc
atttttgtccatggaccaactactgtggagtcgcacggaaactactccacacaggttggagccactcaggcaggag
attcagcatcactcctgcggcgccttcatacacactaaagcttggagaatatggagaggtgacagtggactgtgaacc
acggtcaggattgacaccaatgcatactacgtgatgactgttggaacaaagacgttcttggtccatcgtgagtggttca
tggacctcaacctccttggagcagtgctggaagtactgtgtggaggaacagagagacgttaatggagtttgaggaa
ccacacgccacgaagcagtctgtgatagcattgggctcacaagagggagctctgcatcaagctttggctggagccatt
cctgtggaattttcaagcaacactgtcaagttgacgtcgggtcatttgaagtgtagagtgaagatggaaaaattgcagtt
gaagggaacaacctatggcgtctgttcaaaggctttcaagtttcttgggactcccgcagacacaggtcacggcactgt
ggtgttggaattgcagtacactggcacggatggaccttgcaaagttcctatctcgtcagtggcttcattgaacgacctaa
cgccagtgggcagattggtcactgtcaaccctttgtttcagtggccacggccaacgctaaggtcctgattgaattggaa
ccacccttggagactcatacatagtggtgggcagaggagaacaacagatcaatcaccattggcacaagtctggaa
gcagcattggcaaagcctttacaaccacccctcaaaggagcgcagagactagccgctctaggagacacagcttggg
actttggatcagttggagggtgttcacctcagttgggaaggctgtctaa

Figure 2

MRVVFVVLLLLVAPAYSFNCLGMSNRDFLEGVSGATWVDLVLEGDSCVTIMSKDKP
TIDVKMMNMEAVNLAEVRSYCYLATVSDLSTKAACPTMGEAHNDKRADPAFVCRQ
GVVDRGWGNGCGLFGKGSIDTCAKFACSTKAIGRTILKENIKYEVAIFVHGPTTVES
HGNYSTQVGATQAGRFSITPAAPSYTLKLGEYGEVTVDCEPRSGIDTNAYYVMTVG
TKTFLVHREWFMDLNLPWSSAGSTVWRNRETLMEFEEPHATKQSVIALGSQEGAL
HQALAGAIPVEFSSNTVKLTSGHLKCRVKMEKLQLKGTTYGVCSKAFKFLGTPADT
GHGTVVLELQYTGTDGPCKVPISSVASLNDLTPVGRLVTVNPFVSVATANAKVLIEL
EPPFGDSYIVVGRGEQQINHHWHKSGSSIGKAFTTTLKGAQRLAALGDTAWDFGSV
GGVFTSVGKAV

Figure 3 atgcaaaagaaaagaggaggaaagaccggaattgcagtcatgattggcctgatcgccagcgtaggagcagttacc
ctctctaacttccaagggaaggtgatgatgacggtaaatgctactgacgtcacagatgtcatcacgattccaacagctg
ctggaaagaacctatgcattgtcagagcaatggatgtgggatacatgtgcgatgatactatcacttatgaatgcccagt
gctgtcggctggtaatgatccagaagacatcgactgttggtgcacaaagtcagcagtctacgtcaggtatggaagatg
caccaagacacgccactcaagacgcagtcggaggtcactgacagtgcagacacacggagaaagcactctagcg
aacaagaagggggcttggatggacagcaccaaggccacaaggtatttggtaaaaacagaatcatggatcttgagg
aaccctggatatgccctggtggcagccgtcattggttggatgcttgggagcaacaccatgcagagagttgtgtttgtcgt
gctattgcttttggtggccccagcttacagcttcaactgccttggaatgagcaacagagacttcttggaaggagtgtctgg
agcaacatgggtggatttggttctcgaaggcgacagctgcgtgactatcatgtctaaggacaagcctaccatcgatgtg
aagatgatgaatatggaggcggtcaacctggcagaggtccgcagttattgctatttggctaccgtcagcgatctctcca
ccaaagctgcgtgcccgaccatgggagaagctcacaatgacaaacgtgctgacccagcttttgtgtgcagacaagg
agtggtggacaggggctggggcaacggctgcggattatttggcaaaggaagcattgacacatgcgccaaatttgcct
gctctaccaaggcaataggaagaaccatcttgaaagagaatatcaagtacgaagtggccattttgtccatggaccaa
ctactgtggagtcgcacggaaactactccacacaggttggagccactcaggcagggagattcagcatcactcctgcg
gcgccttcatacacactaaagcttggagaatatggagaggtgacagtggactgtgaaccacggtcagggattgacac
caatgcatactacgtgatgactgttggaacaaagacgttcttggtccatcgtgagtggttcatggacctcaacctcccttg
gagcagtgctggaagtactgtgtggaggaacagagagacgttaatggagtttgaggaaccacacgccacgaagca
gtctgtgatagcattgggctcacaagagggagctctgcatcaagctttggctggagccattcctgtggaattttcaagca
acactgtcaagttgacgtcggtcatttgaagtgtagagtgaagatggaaaaattgcagttgaagggaacaacctatg
gcgtctgttcaaaggctttcaagtttcttgggactcccgcagacacaggtcacggcactgtggtgttggaattgcagtac
actggcacggatggaccttgcaaagttcctatctcgtcagtggcttcattgaacgacctaacgccagtgggcagattgg
tcactgtcaacccttttgtttcagtggccacggccaacgctaaggtcctgattgaattggaaccaccctttggagactcat
acatagtggtgggcagaggagaacaacagatcaatcaccattggcacaagtctggaagcagcattggcaaagcctt
tacaaccaccctcaaaggagcgcagagactagccgctctaggagacacagcttgggactttggatcagttggaggg
gtgttcacctcagttgggaaggctgtccatcaagtgttcggaggagcattccgctcactgttcggaggcatgtcctggat
aacgcaaggattgctgggggctctcctgttgtggatgggcatcaatgctcgtgataggtccatagctctcacgtttctcgc
agttggaggagttctgctcttcctctccgtgaacgtgcacgcttaa

Figure 4

MQKKRGGKTGIAVMIGLIASVGAVTLSNFQGKVMMTVNATDVTDVITIPTAAGKNLCI
VRAMDVGYMCDDTITYECPVLSAGNDPEDIDCWCTKSAVYVRYGRCTKTRHSRRS
RRSLTVQTHGESTLANKKGAWMDSTKATRYLVKTESWILRNPGYALVAAVIGWML
GSNTMQRVVFVVLLLLVAPAYSFNCLGMSNRDFLEGVSGATWVDLVLEGDSCVTIM
SKDKPTIDVKMMNMEAVNLAEVRSYCYLATVSDLSTKAACPTMGEAHNDKRADPA
FVCRQGVVDRGWGNGCGLFGKGSIDTCAKFACSTKAIGRTILKENIKYEVAIFVHGP
TTVESHGNYSTQVGATQAGRFSITPAAPSYTLKLGEYGEVTVDCEPRSGIDTNAYY
VMTVGTKTFLVHREWFMDLNLPWSSAGSTVWRNRETLMEFEEPHATKQSVIALGS
QEGALHQALAGAIPVEFSSNTVKLTSGHLKCRVKMEKLQLKGTTYGVCSKAFKFLG
TPADTGHGTVVLELQYTGTDGPCKVPISSVASLNDLTPVGRLVTVNPFVSVATANAK
VLIELEPPFGDSYIVVGRGEQQINHHWHKSGSSIGKAFTTTLKGAQRLAALGDTAWD
FGSVGGVFTSVGKAVHQVFGGAFRSLFGGMSWITQGLLGALLLWMGINARDRSIAL
TFLAVGGVLLFLSVNVHA

Figure 5 atgaggtccatagctctcacgtttctcgcagttggaggagttctgctcttcctctccgtgaacgtgcacgctgacactgggt
gtgccatagacatcagccggcaagagctgagatgtggaagtggagtgttcatacacaatgatgtggaggcttggatg
gaccggtacaagtattaccctgaaacgccacaaggcctagccaagatcattcagaaagctcataaggaaggagtgt
gcggtctacgatcagtttccagactggagcatcaaatgtggaagcagtgaaggacgagctgaacactcttttgaag
gagaatggtgtggaccttagtgtcgtggttgagaaacaggagggaatgtacaagtcagcacctaaacgcctcaccgc
caccacggaaaaattggaaattggctggaaggcctggggaaagagtattttatttgcaccagaactcgccaacaaca
cctttgtggttgatggtccggagaccaaggaatgtccgactcagaatcgcgcttggaatagcttagaagtggaggatttt
ggatttggtctcaccagcactcggatgttcctgaaggtcagagagagcaacacaactgaatgtgactcgaagatcatt
ggaacggctgtcaagaacaacttggcgatccacagtgacctgtcctattggattgaaagcaggctcaatgatacgtgg
aagcttgaaagggcagttctgggtgaagtcaaatcatgtacgtggcctgagacgcataccttgtgggcgatggaatc
cttgagagtgacttgataataccagtcacactggcgggaccacgaagcaatcacaatcggagacctgggtacaaga
cacaaaaccagggcccatgggacgaaggccgggtagagattgacttcgattactgcccaggaactacggtcaccct
gagtgagagctgcggacaccgtggacctgccactcgcaccaccacagagagcggaaagttgataacagattggtg
ctgcaggagctgcaccttaccaccactgcgctaccaaactgacagcggctgttggtatggtatggagatcagaccac
agagacatgatgaaaagacctaatga

Figure 6

MRSIALTFLAVGGVLLFLSVNVHADTGCAIDISRQELRCGSGVFIHNDVEAWMDRYK
YYPETPQGLAKIIQKAHKEGVCGLRSVSRLEHQMWEAVKDELNTLLKENGVDLSVV
VEKQEGMYKSAPKRLTATTEKLEIGWKAWGKSILFAPELANNTFVVDGPETKECPT
QNRAWNSLEVEDFGFGLTSTRMFLKVRESNTTECDSKIIGTAVKNNLAIHSDLSYWI
ESRLNDTWKLERAVLGEVKSCTWPETHTLWGDGILESDLIPVTLAGPRSNHNRRP
GYKTQNQGPWDEGRVEIDFDYCPGTTVTLSESCGHRGPATRTTTESGKLITDWCC
RSCTLPPLRYQTDSGCWYGMEIRPQRHDEKT

Figure 7 atgaacaggaggaaaagatccgtgaccatgctcctcatgctgctgcccacagtcctggctttccatttgaccacacga
gggggagagccacacatgatagttagtaagcaggaaagaggaaagtcactcttgttcaagacctctgcaggtgtca
atatgtgcactctcattgcgatggatttgggagagttatgtgaggacacaatgacttacaaatgccccggatcactgag
gcggaaccagatgacgttgactgctggtgcaatgccacagacacatgggtgacctatgggacgtgttctcaaaccgg
tgaacaccgacgagacaaacgttccgtggcactggcccacacgtgggacttggtctagaaacaagaaccgaaac
atggatgtcctctgaaggcgcctggaaacaaatacaaaaagtggagacttgggctttgagacacccaggattcacgg
tgatagctcttttttttagcacatgccataggaacatccatcactcagaaagggatcattttcattctgctgatgctggtaaca
ccatcaatggccatgcgatgcgtgggaataggcaacagagacttcgttgaaggactgtcaggagcaacgtgggtgg
acgtggtattggagcatggaagctgcgtcaccaccatggcaaaaaataaaccaacattggacattgaactcttgaag
acggaggtcacgaaccctgccgtcttgcgcaaattgtgcattgaagctaaaatatcaaacaccaccaccgattcaag
atgtccaacacaaggagaggctacactggtggaagaacaagacgcgaactttgtgtgtcgacgaacggttgtggac
agaggctggggcaatggctgcggactatttggaaaaggaagcctactgacgtgtgctaagttcaagtgtgtgacaaa
actggaaggaaagatagttcaatatgaaaacttaaaatattcagtgatagtcactgtccacacaggggaccagcacc
aggtgggaaacgagactacagaacatggaacaattgcaaccataacacctcaagctcctacgtcgaaatacagtt
gacagactacggaacccttacactggactgctcacccagaacagggctggactttaatgaggtggtgctattgacaat
gaaagaaaaatcatggcttgtccacaaacaatggtttctagacttaccactgccttggacttcggggcttcaacatccc
aagagacttggaacagacaagatttgctggtcacattcaagacagctcatgcaaagaagcaggaagtagtcgtact
gggatcacaggaaggagcaatgcacactgcgttgaccggggcgacagaaatccagacgtcaggaacgacaaca
atctttgcaggacacctgaaatgcagattaaaaatggataaactgactttaaaagggatgtcatatgtgatgtgcacag
gctcatttaagctagagaaggaagtggctgagacccagcatggaactgtcctagtgcaggttaaatacgaaggaac
agatgcgccatgcaagatcccctttcgacccaagatgagaaaggagtgacccagaatgggagattgataacagcc
aatcccatagttactgacaaagaaaaaccaatcaacattgagacagaaccaccttttggtgagagctacatcatagta
ggggcaggtgaaaaagcttgaaactaagctggttcaagaaaggaagcagcatagggaaaatgttcgaagcaatc
gcccgaggagcacgaaggatggctatcctgggagacaccgcatgggacttcggctctataggaggagtgtttacgtc
tgtgggaaaattggtacaccaggttttggaaccgcatacggggtcctgttcagcggcgtttcttggaccatgaaaatag
gaatagggatcttgctgacatggttgggattaaattcaaggagcgcgtcgctttcgatgacgtgcattgcagttggcatg
gttacactgtacctaggagtcatggtttaa

Figure 8

MNRRKRSVTMLLMLLPTVLAFHLTTRGGEPHMIVSKQERGKSLLFKTSAGVNMCTLI
AMDLGELCEDTMTYKCPRITEAEPDDVDCWCNATDTWVTYGTCSQTGEHRRDKR
SVALAPHVGLGLETRTETWMSSEGAWKQIQKVETWALRHPGFTVIALFLAHAIGTSI
TQKGIIFILLMLVTPSMAMRCVGIGNRDFVEGLSGATWVDVVLEHGSCVTTMAKNKP
TLDIELLKTEVTNPAVLRKLCIEAKISNTTTDSRCPTQGEATLVEEQDANFVCRRTVV
DRGWGNGCGLFGKGSLLTCAKFKCVTKLEGKIVQYENLKYSVIVTVHTGDQHQVG
NETTEHGTIATITPQAPTSEIQLTDYGTLTLDCSPRTGLDFNEVVLLTMKEKSWLVHK
QWFLDLPLPWTSGASTSQETWNRQDLLVTFKTAHAKKQEVVVLGSQEGAMHTALT
GATEIQTSGTTTIFAGHLKCRLKMDKLTLKGMSYVMCTGSFKLEKEVAETQHGTVLV
QVKYEGTDAPCKIPFSTQDEKGVTQNGRLITANPIVTDKEKPINIETEPPFGESYIIVG
AGEKALKLSWFKKGSSIGKMFEAIARGARRMAILGDTAWDFGSIGGVFTSVGKLVH
QVFGTAYGVLFSGVSWTMKIGIGILLTWLGLNSRSASLSMTCIAVGMVTLYLGVMV

DENGUE AND WEST NILE VIRUSES PROTEINS AND GENES CODING THE FOREGOING, AND THEIR USE IN VACCINAL, THERAPEUTIC AND DIAGNOSTIC APPLICATIONS

This application is a continuation of application Ser. No. 11/210,960, filed Aug. 25, 2005 (now U.S. Pat. No. 7,556,812), which is a continuation of PCT International Application No. PCT/IB2004/001027, filed Feb. 26, 2004, which claims priority to Canadian Patent Application No. 2,420,092 filed Feb. 26, 2003, and Canadian Patent Application No. 2,432,738, filed Jun. 20, 2003.

FIELD OF THE INVENTION

The present invention relates to West-Nile virus (WNV) and/or Dengue virus derived peptides, and more particularly to polypeptides or polynucleotides derived from WNV and/or Dengue virus polypeptides or polynucleotides and their use in the preparation of compositions and vaccines. More specifically, the present invention is concerned with compositions, vaccines and methods for providing an immune response and/or a protective immunity to animals against a West-Nile virus or a Dengue virus and methods for the diagnosis of West-Nile virus or Dengue virus infection.

BACKGROUND OF THE INVENTION

Flaviviridae are arboviruses (arthropod-borne virus) mainly transported by mosquitoes and blood-sucking ticks. They are small encapsidated viruses and their genomes consist of infectious single-stranded and linear RNA of positive polarity. In Man, *flaviviruses* cause deadly hemorrhagic fever or meningoencephalitis. Yellow fever, dengue fever and Japanese encephalitis are the main tropical flaviviroses. Other important human flaviviroses are Saint Louis encephalitis, tick-born European encephalitis and West Nile fever.

West Nile fever is a zoonosis associated with a *flavivirus* which was first isolated in Uganda in 1937. Its transmission cycle calls for birds as the main reservoir and for blood sucking mosquitoes of the *Culex* genus as vectors. Migratory viremic birds transport the virus to far-away regions where they transmit it anew to ornithophile mosquitoes of the *Culex* genus. Many species of mammals are permissive for the West Nile virus. Horses are particularly sensitive to the disease but do not participate in the cycle of transmission. West Nile fever is endemic in Africa, Asia, Europe and Australia. Phylogenic studies have revealed the existence of two strains of viruses: viral line 1 has a worldwide distribution, and viral line 2 is essentially African. Viral line 1 was responsible for enzooties in Romania (1996), Russia (1999), Israel (1998-2000) and more recently in North America where the virus had never been detected before 1999. The viral strains isolated during the recent epidemics in Israel and the United-States are more than 99.7% identical. In the Middle-East and North America, where the virus has taken root, an important bird mortality rate has been observed among infected birds, notably in Corvidae. In North America, over 4000 subjects were infected with the West Nile virus, 250 of which died between the months of August and December 2002. At the present time, zoonosis is observed in all regions of the United States. At the moment, there exists no human vaccine or specific therapy against West Nile fever.

In temperate and sub-tropical regions, human infections may occur during the fall season. When a subject is bitten by an infected mosquito, the incubation period lasts approximately one week but less than 20% of people infected with the West Nile virus ever go on to clinical manifestations. In its benignant form, the viral infection manifests itself by an undifferentiated febrile state associated with muscular weakness, headaches and abdominal pain. In less than 1% of infected subjects, encephalitis or acute aseptic meningitis may occur. Splenomegaly, hepatitis, pancreatitis and myocarditis are also observed. Flask paralyses similar to a poliomyelitic syndrome have recently been reported, but fatal cases of viral encephalitis (5% of patients having severe neurological disorders) mainly concern fragile subjects and the aged. Inter-human transmission of the virus has also recently been observed in the United-States in subjects having undergone organ transplants or having been perfused with contaminated blood products. Intra-uterine transmission of the virus has been reported in the United-States. The development of a human vaccine against the West Nile fever is a priority in view of the fact that the zoonosis has taken root in North America and is expected to propagate in the coming months to Central America, South America and the Caribbean where dengue fever and yellow fever are already rampant.

Therefore, there is a need for West-Nile virus (WNV) and/or Dengue virus derived peptides, and more particularly to polypeptides or polynucleotides derived from WNV and/or Dengue virus polypeptides or polynucleotides and their use in the preparation of compositions and vaccines.

The present invention fulfils these needs and also other needs which will be apparent to those skilled in the art upon reading the following specification.

SUMMARY OF THE INVENTION

The present invention relates to West-Nile virus and/or Dengue virus derived polypeptides.

More specifically, one object of the invention concerns a purified polypeptide wherein it derives from a West-Nile virus antigen or a Dengue virus antigen.

Another object of the invention concerns a purified polyclonal or monoclonal antibody capable of specifically binding to a polypeptide of the invention.

Another object of the invention concerns a purified polynucleotide sequence coding for the polypeptide of the invention and its use for detecting the presence or absence of a West-Nile virus antigen or a Dengue virus antigen in a biological sample.

A further object of the invention concerns a recombinant viral vector which is a recombinant virus comprising a polynucleotide sequence of the invention.

Another object of the invention is a recombinant measles virus capable of expressing a polypeptide of the invention or comprising, in its genome, a polynucleotide of the invention.

Yet, another object of the invention relates to a pharmaceutical composition comprising:

a) at least one component selected from the group consisting of:
   a polypeptide of the invention or a functional derivative thereof;
   an antibody as defined above;
   an expression vector as defined above;
   a polynucleotide of the invention or a fragment thereof,
   a recombinant viral vector of the invention; and
   a recombinant measles virus of the invention;
   and
b) a pharmaceutically acceptable vehicle or carrier.

Another object of the invention concerns the use of the pharmaceutical composition of the invention, as an anti- West-Nile virus and/or an anti-Dengue virus agent, or for the preparation of an anti-West-Nile virus and/or an anti-Dengue virus vaccine.

Another object of the invention relates to a host cell incorporating an expression vector as defined above or a recombinant viral vector as defined above.

Furthermore, another object of the invention concerns a method of producing a recombinant virus for the preparation of an anti-West-Nile virus vaccine or an anti-Dengue virus vaccine, the method comprising the steps of:
a) providing a host cell as defined above;
b) placing the host cell from step a) in conditions permitting the replication of a recombinant virus capable of expressing a polypeptide of the invention; and
c) isolating the recombinant virus produced in step b).

Another object of the invention concerns a West-Nile virus neutralization assay, comprising the steps of:
a) contacting VERO cells with West-Nile virus and an antibody;
b) culturing said VERO cells under conditions which allow for West-Nile virus replication; and
c) measuring reduction of West-Nile virus replication foci on said VERO cells.

A further object of the invention is to provide a method for treating and/or preventing a WNV- or Dengue virus-associated disease or infection in an animal, the method comprising the step of administering to the animal an effective amount of at least one element selected from the group consisting of:
a polypeptide or a functional derivative thereof as defined above;
an antibody as defined above;
an expression vector as defined above;
a polynucleotide or a fragment thereof as defined above;
a recombinant viral vector as defined above; and
a recombinant measles virus as defined above.

BRIEF DESCRIPTION OF THE DRAWINGS

FIG. 1 shows the nucleic acid sequence encoding the secreted glycoprotein E from WNV and identified as SEQ ID NO. 1.

FIG. 2 shows the amino acid sequence of the secreted glycoprotein E from WNV and identified as SEQ ID NO 5.

FIG. 3 shows the nucleic acid sequence encoding the preM plus E glycoproteins from WNV and identified as SEQ ID NO. 2.

FIG. 4 shows the amino acid sequence of the preM plus E glycoproteins from WNV and identified as SEQ ID NO 6.

FIG. 5 shows the nucleic acid sequence encoding the NS1 protein from WNV and identified as SEQ ID NO. 3.

FIG. 6 shows the amino acid sequence of the NS1 protein from WNV and identified as SEQ ID NO 7.

FIG. 7 shows the nucleic acid sequence encoding the preM-E gene from Dengue type 1 virus and identified as SEQ ID NO. 4.

FIG. 8 shows the amino acid sequence of the preM-E gene from Dengue type 1 virus and identified as SEQ ID NO 8.

FIG. 9 is a schematic map of the pTM-MVSchw recombinant plasmids according to preferred embodiments of the invention.

FIG. 10 shows the expression of sEWNV by MVSchw-sE$_{WNV}$ recombinant MV in Vero cells. (A) Schematic diagram of MV$_{Schw}$-sE$_{WNV}$ and virus growth. The IS-98-ST1 cDNA coding for sE$_{WNV}$ was inserted into the Schwarz MV genome between the BsiW1 and BssHII sites of the ATU at position 2. The MV genes are indicated: N (nucleoprotein), PVC (phosphoprotein and V, C proteins), M (matrix), F (fusion), H (hemagglutinin), L (polymerase). T7: T7 RNA polymerase promoter; hh: hammerhead ribozyme, T7t: T7 RNA polymerase terminator; δ: hepatitis delta virus (HDV) ribozyme; ATU: additional transcription unit. (B) Growth curves of MV. Vero cells were infected with MV$_{Schw}$ (open box) or MV$_{Schw}$-sE$_{WNV}$ (black box) at a multiplicity of infection (m.o.i) of 0.01 TCID$_{50}$/cell. At various times post-infection, infectious virus particles were titered as described in the Methods. (C) Immunofluorescence staining of sE$_{WNV}$ glycoprotein in syncitia of MV$_{Schw}$-sE$_{WNV}$-infected Vero cells fixed 36 h post-infection. Cells were permeabilized (A, B) or not (C, D) with Triton X-100 and then immunostained using anti-WNV HMAF. Magnification: ×1000. No positive signal was observed in MV$_{Schw}$-infected cells. (D) Radioimmunoprecipitation (RIP) assay showing the release of sE$_{WNV}$ from MV$_{Schw}$-sE$_{WNV}$-infected cells. Vero cells were infected with WNV strain IS-98-ST1 (m.o.i of 5) for 24 h, MV$_{Schw}$ (m.o.i. of 0.1), MV$_{Schw}$-sE$_{WNV}$ (m.o.i. of 0.1) for 40 h, or mock-infected (MI). Radiolabeled supernatants and cell lysates were immunoprecipitated with specific anti-MV (α-MV) or anti-WNV (α-WNV) polyclonal antibodies. WNV E glycoprotein (open arrow head) and sE$_{WNV}$ (black arrow head) are shown.

FIG. 11 shows anti-MVSchw-sE$_{WNV}$ antibodies recognizing the WNV E glycoprotein. Vero cells were infected with WNV strain IS-98-ST1 (WNV) or mock-infected (No virus). Labeled cell lysates were immunoprecipitated with pooled immune sera (dilution 1:100) from mice inoculated with WNV, MVSchw, MVSchw-sE$_{WNV}$ as described in the legend to FIG. 10D. Specific anti-lymphochoriomeningitis virus (LCMV) antibodies were used as a negative control. WNV structural glycoproteins prM and E and non structural proteins NS3, NS5, NS2A and NS2B are shown. p.c., post-challenge.

DETAILED DESCRIPTION OF THE INVENTION

The present invention relates to West-Nile virus (WNV) and/or Dengue virus derived peptides, and more particularly to polypeptides or polynucleotides derived from WNV and/or Dengue virus polypeptides or polynucleotides and their use in the preparation of compositions and vaccines. More specifically, the present invention is concerned with compositions, vaccines and methods for providing an immune response and/or a protective immunity to animals against a West-Nile virus or a Dengue virus and methods for the diagnosis of West-Nile virus or Dengue virus infection.

As used herein, the term "immune response" refers to the T cell response or the increased serum levels of antibodies to an antigen, or presence of neutralizing antibodies to an antigen, such as a WNV or a Dengue virus antigen. The term "immune response" is to be understood as including a humoral response and/or a cellular response and/or an inflammatory response.

An "antigen" refers to a molecule, such as a protein or a polypeptide, containing one or more epitopes that will stimulate a host's immune system to make a humoral and/or cellular antigen-specific response. The term is also used interchangeably with "immunogen".

The term "protection" or "protective immunity" refers herein to the ability of the serum antibodies and cellular response induced during immunization to protect (partially or totally) against a West-Nile virus or a Dengue virus. Thus, an animal immunized by the compositions or vaccines of the invention will experience limited growth and spread of an infectious WNV or Dengue virus.

As used herein, the term "animal" refers to any animal that is susceptible to be infected by a West-Nile virus or a Dengue virus. Among the animals which are known to be potentially infected by these viruses, there are, but not limited to, humans, birds and horses.

1. Polynucleotides and Polypeptides

In a first embodiment, the present invention concerns a purified polypeptide characterized in that it derives from a West-Nile virus antigen or a Dengue virus antigen or functional derivative thereof. As can be appreciated, a protein/peptide is said to "derive" from a protein/peptide or from a fragment thereof when such protein/peptide comprises at least one portion, substantially similar in its sequence, to the native protein/peptide or to a fragment thereof.

The West-Nile virus antigen of the present invention is preferably selected from the group consisting of secreted envelope glycoprotein (E), heterodimer glycoproteins (PreM-E) and NS1 protein. More specifically, the secreted envelope glycoprotein (E) comprises the sequence of SEQ ID NO: 5 or a functional derivative thereof, the heterodimer glycoproteins (PreM-E) comprises the sequence of SEQ ID NO: 6 or a functional derivative thereof, and the NS1 protein comprises the sequence of SEQ ID NO: 7 or a functional derivative thereof.

The Dengue virus antigen of the invention is preferably selected from the group consisting of secreted envelope glycoprotein (E), heterodimer glycoproteins (PreM-E) and NS1 protein. More specifically, the heterodimer glycoproteins (PreM-E) comprises the sequence of SEQ ID NO: 8 or a functional derivative thereof.

According to a preferred embodiment, the polypeptide of the present invention has an amino acid sequence having at least 80% homology, or even preferably 85% homology to part or all of SEQ ID NO:1, of SEQ ID NO:2, of SEQ ID NO:3 or of SEQ ID NO:4.

A "functional derivative", as is generally understood and used herein, refers to a protein/peptide sequence that possesses a functional biological activity that is substantially similar to the biological activity of the whole protein/peptide sequence. In other words, it refers to a polypeptide or fragment(s) thereof that substantially retain the same biological functions as the polypeptide of SEQ ID Nos: 5 to 8. A functional derivative of a protein/peptide may or may not contain post-translational modifications such as covalently linked carbohydrate, if such modification is not necessary for the performance of a specific function. The term "functional derivative" is intended to the "fragments", "segments", "variants", "analogs" or "chemical derivatives" of a protein/peptide. As used herein, a protein/peptide is said to be a "chemical derivative" of another protein/peptide when it contains additional chemical moieties not normally part of the protein/peptide, said moieties being added by using techniques well known in the art. Such moieties may improve the protein/peptide solubility, absorption, bioavailability, biological half life, and the like. Any undesirable toxicity and side-effects of the protein/peptide may be attenuated and even eliminated by using such moieties.

Yet, more preferably, the polypeptide comprises an amino acid sequence substantially the same or having 100% identity with SEQ ID NO:1, SEQ ID NO:2, SEQ ID NO:3, or SEQ ID NO:4.

One can use a program such as the CLUSTAL program to compare amino acid sequences. This program compares amino acid sequences and finds the optimal alignment by inserting spaces in either sequence as appropriate. It is possible to calculate amino acid identity or homology for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

As used herein, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene-encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation, selenoylation, sulfation and transfer-RNA mediated addition of amino acids to proteins, such as arginylation, and ubiquitination. See, for instance: PROTEINS—STRUCTURE AND MOLECULAR PROPERTIES, 2nd Ed., T. E. Creighton, W.H. Freeman and Company, New York (1993); Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York (1983); Seifter et al., Meth. Enzymol. 182:626-646 (1990); and Rattan et al., Protein Synthesis: Posttranslational Modifications and Aging, Ann. N.Y. Acad. Sci. 663: 48-62 (1992). Polypeptides may be branched or cyclic, with or without branching. Cyclic, branched and branched circular polypeptides may result from post-translational natural processes and may be made by entirely synthetic methods, as well.

With respect to protein or polypeptide, the term "isolated polypeptide" or "isolated and purified polypeptide" is sometimes used herein. This term refers primarily to a protein produced by expression of an isolated polynucleotide molecule contemplated by invention. Alternatively, this term may refer to a protein which has been sufficiently separated from other proteins with which it would naturally be associated, so as to exist in "substantially pure" form.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest.

Purity is measured by methods appropriate for the compound of interest (e.g. chromatographic methods, agarose or polyacrylamide gel electrophoresis, HPLC analysis, and the like).

In a second embodiment, the present invention concerns a purified polynucleotide encoding a polypeptide of the invention. Therefore, the polynucleotide of the invention has a nucleic acid sequence which is at least 65% identical, more particularly 80% identical and even more particularly 95% identical to part or all of any one of SEQ ID NO 5 to 8 or functional fragments thereof.

A "functional fragment", as is generally understood and used herein, refers to a nucleic acid sequence that encodes for a functional biological activity that is substantially similar to the biological activity of the whole nucleic acid sequence. In other words, it refers to a nucleic acid or fragment(s) thereof that substantially retains the capacity of encoding for a polypeptide of the invention.

The term "fragment" as used herein refer to a polynucleotide sequence (e.g., cDNA) which is an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art.

With reference to polynucleotides of the invention, the term "isolated polynucleotide" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated polynucleotide" may comprise a DNA molecule inserted into a vector, such as a plasmid or virus vector, or integrated into the genomic DNA of a procaryote or eucaryote. An "isolated polynucleotide molecule" may also comprise a cDNA molecule.

Amino acid or nucleotide sequence "identity" and "similarity" are determined from an optimal global alignment between the two sequences being compared. An optimal global alignment is achieved using, for example, the Needleman-Wunsch algorithm (Needleman and Wunsch, 1970, J. Mol. Biol. 48:443-453). "Identity" means that an amino acid or nucleotide at a particular position in a first polypeptide or polynucleotide is identical to a corresponding amino acid or nucleotide in a second polypeptide or polynucleotide that is in an optimal global alignment with the first polypeptide or polynucleotide. In contrast to identity, "similarity" encompasses amino acids that are conservative substitutions. A "conservative" substitution is any substitution that has a positive score in the blosum62 substitution matrix (Hentikoff and Hentikoff, 1992, Proc. Natl. Acad. Sci. USA 89: 10915-10919). By the statement "sequence A is n % similar to sequence B" is meant that n % of the positions of an optimal global alignment between sequences A and B consists of identical residues or nucleotides and conservative substitutions. By the statement "sequence A is n % identical to sequence B" is meant that n % of the positions of an optimal global alignment between sequences A and B consists of identical residues or nucleotides.

As used herein, the term "polynucleotide(s)" generally refers to any polyribonucleotide or poly-deoxyribonucleotide, which may be unmodified RNA or DNA or modified RNA or DNA. This definition includes, without limitation, single- and double-stranded DNA, DNA that is a mixture of single- and double-stranded regions or single-, double- and triple-stranded regions, cDNA, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. "Polynucleotide(s)" embraces short polynucleotides or fragments comprising at least 6 nucleotides often referred to as oligonucleotide(s). The term "polynucleotide(s)" as it is employed herein thus embraces such chemically, enzymatically or metabolically modified forms of polynucleotides, as well as the chemical forms of DNA and RNA characteristic of viruses and cells, including, for example, simple and complex cells which exhibits the same biological function as the polypeptide encoded by any one of SEQ ID NOS. 1 to 4. The term "polynucleotide(s)" also embraces, short nucleotides or fragments, often referred to as "oligonucleotides", that due to mutagenesis are not 100% identical but nevertheless code for the same amino acid sequence.

2. Vectors and Cells

In a third embodiment, the invention is also directed to a host, such as a genetically modified cell, comprising any of the polynucleotide sequence according to the invention and more preferably, a host capable of expressing the polypeptide encoded by this polynucleotide. Even more preferably, the present invention is concerned with a host cell that incorporates an expression vector or a recombinant viral vector as defined herein below.

The host cell may be any type of cell (a transiently-transfected mammalian cell line, an isolated primary cell, or insect cell, yeast (*Saccharomyces cerevisiae, Ktuyveromyces lactis, Pichia pastoris*), plant cell, microorganism, or a bacterium (such as *E. coli*). The following biological deposit relating to MEF/3T3.Tet-Off/prME.WN # h2 cell line comprising an expression vector encoding for pseudo-particles of WNV strain IS-98-ST1 composed of prME complexed glycoproteins was registered at the Collection Nationale des Cultures de Microorganismes (CNCM) under accession numbers I-3018 on May 2, 2003.

In a fourth embodiment, the invention is further directed to cloning or expression vector comprising a polynucleotide sequence as defined above.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector.

A number of vectors suitable for stable transfection of cells and bacteria are available to the public (e.g. plasmids, adenoviruses, baculoviruses, yeast baculoviruses, plant viruses, adeno-associated viruses, retroviruses, Herpes Simplex Viruses, Alphaviruses, Lentiviruses), as are methods for constructing such cell lines. It will be understood that the present invention encompasses any type of vector comprising any of the polynucleotide molecule of the invention.

According to a preferred embodiment, the vector is a recombinant viral vector which is a recombinant virus comprising a polynucleotide sequence as defined above. Preferably the recombinant virus is a live attenuated virus or a defective virus, such as a recombinant virus selected from the group consisting of measles virus, hepatitis B virus, human papillomavirus, picornaviridae and lentivirus. More preferably, the recombinant virus is a recombinant measles virus, for instance the Schwarz measles virus strain, which is capable of expressing a polypeptide as defined above or comprises, in its genome, a polynucleotide as defined above.

3. Antibodies

In a fifth embodiment, the invention features purified antibodies that specifically bind to the isolated or purified polypeptide as defined above or fragments thereof. The antibodies of the invention may be prepared by a variety of methods using the polypeptides described above. For example, the West-Nile or Dengue virus antigen, or antigenic fragments thereof, may be administered to an animal in order to induce the production of polyclonal antibodies. Alternatively, antibodies used as described herein may be monoclonal antibodies, which are prepared using hybridoma technology (see, e.g., Hammerling of al., In Monoclonal Antibodies and T-Cell Hybridomas, Elsevier, NY, 1981).

As mentioned above, the present invention is preferably directed to antibodies that specifically bind to a West-Nile antigen or a Dengue virus antigen, or fragments thereof. In particular, the invention features "neutralizing" antibodies. By "neutralizing" antibodies is meant antibodies that interfere with any of the biological activities of any of the WNV antigen or Dengue virus antigen. Any standard assay known to one skilled in the art may be used to assess potentially neutralizing antibodies. Once produced, monoclonal and polyclonal antibodies are preferably tested for specific WNV or Dengue virus proteins recognition by Western blot, immunoprecipitation analysis or any other suitable method.

Antibodies that recognize WNV or Dengue virus proteins expressing cells and antibodies that specifically recognize WNV or Dengue virus proteins (or functional fragments thereof), such as those described herein, are considered useful to the invention. Such an antibody may be used in any standard immunodetection method for the detection, quantification, and purification of WNV or Dengue virus proteins. The antibody may be a monoclonal or a polyclonal antibody and may be modified for diagnostic purposes. The antibodies of the invention may, for example, be used in an immunoassay to monitor WNV or Dengue virus proteins expression levels, to determine the amount of WNV or Dengue virus proteins or fragment thereof in a biological sample and evaluate the presence or not of a WNV or Dengue virus. In addition, the antibodies may be coupled to compounds for diagnostic and/or therapeutic uses such as gold particles, alkaline phosphatase, peroxidase for imaging and therapy. The antibodies may also be labeled (e.g. immunofluorescence) for easier detection.

With respect to antibodies of the invention, the term "specifically binds to" refers to antibodies that bind with a relatively high affinity to one or more epitopes of a protein of interest, but which do not substantially recognize and bind molecules other than the one(s) of interest. As used herein, the term "relatively high affinity" means a binding affinity between the antibody and the protein of interest of at least $10^6$ $M^{-1}$, and preferably of at least about $10^7$ $M^{-1}$ and even more preferably $10^8$ $M^{-1}$ to $10^{10}$ $M^{-1}$. Determination of such affinity is preferably conducted under standard competitive binding immunoassay conditions which is common knowledge to one skilled in the art. As used herein, "antibody" and "antibodies" include all of the possibilities mentioned hereinafter: antibodies or fragments thereof obtained by purification, proteolytic treatment or by genetic engineering, artificial constructs comprising antibodies or fragments thereof and artificial constructs designed to mimic the binding of antibodies or fragments thereof. Such antibodies are discussed in Colcher at al. (*Q J Nucl Med* 1998; 42: 225-241). They include complete antibodies, F(ab')$_2$ fragments, Fab fragments, Fv fragments, scFv fragments, other fragments, CDR peptides and mimetics. These can easily be obtained and prepared by those skilled in the art. For example, enzyme digestion can be used to obtain F(ab')$_2$ and Fab fragments by subjecting an IgG molecule to pepsin or papain cleavage respectively. Recombinant antibodies are also covered by the present invention.

Alternatively, the antibody of the invention may be an antibody derivative. Such an antibody may comprise an antigen-binding region linked or not to a non-immunoglobulin region. The antigen binding region is an antibody light chain variable domain or heavy chain variable domain. Typically, the antibody comprises both light and heavy chain variable domains, that can be inserted in constructs such as single chain Fv (scFv) fragments, disulfide-stabilized Fv (dsFv) fragments, multimeric scFv fragments, diabodies, minibodies or other related forms (Colcher et al. *Q J Nucl Med* 1998; 42: 225-241). Such a derivatized antibody may sometimes be preferable since it is devoid of the Fc portion of the natural antibody that can bind to several effectors of the immune system and elicit an immune response when administered to a human or an animal. Indeed, derivatized antibody normally do not lead to immuno-complex disease and complement activation (type III hypersensitivity reaction).

Alternatively, a non-immunoglobulin region is fused to the antigen-binding region of the antibody of the invention. The non-immunoglobulin region is typically a non-immunoglobulin moiety and may be an enzyme, a region derived from a protein having known binding specificity, a region derived from a protein toxin or indeed from any protein expressed by a gene, or a chemical entity showing inhibitory or blocking activity(ies) against WNV or Dengue virus proteins. The two regions of that modified antibody may be connected via a cleavable or a permanent linker sequence.

Preferably, the antibody of the invention is a human or animal immunoglobulin such as IgG1, IgG2, IgG3, IgG4, IgM, IgA, IgE or IgD carrying rat or mouse variable regions (chimeric) or CDRs (humanized or "animalized"). Furthermore, the antibody of the invention may also be conjugated to any suitable carrier known to one skilled in the art in order to provide, for instance, a specific delivery and prolonged retention of the antibody, either in a targeted local area or for a systemic application.

The term "humanized antibody" refers to an antibody derived from a non-human antibody, typically murine, that retains or substantially retains the antigen-binding properties of the parent antibody but which is less immunogenic in humans. This may be achieved by various methods including (a) grafting only the non-human CDRs onto human framework and constant regions with or without retention of critical framework residues, or (b) transplanting the entire non-human variable domains, but "cloaking" them with a human-like section by replacement of surface residues. Such methods are well known to one skilled in the art.

As mentioned above, the antibody of the invention is immunologically specific to the polypeptide of the present invention and immunological derivatives thereof. As used herein, the term "immunological derivative" refers to a polypeptide that possesses an immunological activity that is substantially similar to the immunological activity of the whole polypeptide, and such immunological activity refers to the capacity of stimulating the production of antibodies immunologically specific to the WNV or Dengue virus proteins or derivative thereof. The term "immunological derivative" therefore encompass "fragments", "segments", "variants", or "analogs" of a polypeptide.

4. Compositions and Vaccines

The polypeptides of the present invention, the polynucleotides coding the same, the polyclonal or monoclonal antibodies, the recombinant measles virus produced according to the invention, may be used in many ways for the diagnosis, the treatment or the prevention of WNV- or Dengue virus-associated diseases or infection.

In a sixth embodiment, the present invention relates to a composition for eliciting an immune response or a protective immunity against a WNV or a Dengue virus. According to a related aspect, the present invention relates to a vaccine for preventing and/or treating a WNV- or Dengue virus-associated disease or infection. As used herein, the term "treating" refers to a process by which the symptoms of a WNV- or Dengue virus-associated disease or infection are alleviated or completely eliminated. As used herein, the term "preventing" refers to a process by which a WNV- or Dengue virus-associated disease or infection is obstructed or delayed. The composition or the vaccine of the invention comprises a polynucleotide, a polypeptide, an expression vector, a recombinant viral vector, a recombinant measles virus and/or an antibody as defined above and an acceptable carrier.

As used herein, the expression "an acceptable carrier" means a vehicle for containing the polynucleotide, the polypeptide, the expression vector, the recombinant viral vector, the recombinant measles virus and/or the antibody of the invention that can be injected into an animal host without adverse effects. Suitable carriers known in the art include, but are not limited to, gold particles, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

Further agents can be added to the composition and vaccine of the invention. For instance, the composition of the invention may also comprise agents such as drugs, immunostimulants (such as α-interferon, β-interferon, γ-interferon, granulocyte macrophage colony stimulator factor (GM-CSF), macrophage colony stimulator factor (M-CSF), interleukin 2 (IL2), interleukin 12 (IL12), and CpG oligonucleotides), antioxidants, surfactants, flavoring agents, volatile oils, buffering agents, dispersants, propellants, and preservatives. For preparing such compositions, methods well known in the art may be used.

The amount of polynucleotide, polypeptide, expression vector, recombinant viral vector, recombinant measles virus and/or antibody present in the compositions or in the vaccines of the present invention is preferably a therapeutically effective amount. A therapeutically effective amount of the polynucleotide, the polypeptide, the expression vector, the recombinant viral vector, the recombinant measles virus and/or the antibody of the invention is that amount necessary to allow the same to perform their immunological role without causing, overly negative effects in the host to which the composition is administered. The exact amount of polynucleotide, polypeptide, expression vector, recombinant viral vector, recombinant measles virus and/or antibody to be used and the composition/vaccine to be administered will vary according to factors such as the type of condition being treated, the mode of administration, as well as the other ingredients in the composition.

5. Methods of Use

In a seventh embodiment, the present invention relates to methods for treating and/or preventing a WNV- or Dengue virus-associated disease or infection in an animal are provided. The method comprises the step of administering to the animal an effective amount of at least one element selected from the group consisting of:
- a polypeptide of the invention or a functional derivative thereof;
- an antibody as defined above;
- an expression vector as defined above;
- a polynucleotide of the invention or a fragment thereof,
- a recombinant viral vector of the invention; and
- a recombinant measles virus of the invention.

The vaccine, antibody and composition of the invention may be given to an animal through various routes of administration. For instance, the composition may be administered in the form of sterile injectable preparations, such as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents. They may be given parenterally, for example intravenously, intramuscularly or sub-cutaneously by injection, by infusion or per os. The vaccine and the composition of the invention may also be formulated as creams, ointments, lotions, gels, drops, suppositories, sprays, liquids or powders for topical administration. They may also be administered into the airways of a subject by way of a pressurized aerosol dispenser, a nasal sprayer, a nebulizer, a metered dose inhaler, a dry powder inhaler, or a capsule. Suitable dosages will vary, depending upon factors such as the amount of each of the components in the composition, the desired effect (short or long term), the route of administration, the age and the weight of the animal to be treated. Any other methods well known in the art may be used for administering the vaccine, antibody and the composition of the invention.

The present invention is also directed to a method of producing a recombinant virus for the preparation of an anti-West-Nile virus vaccine or an anti-Dengue virus vaccine, the method comprising the steps of:
a) providing a host cell as defined above;
b) placing the host cell from step a) in conditions permitting the replication of a recombinant virus capable of expressing a polypeptide according to the invention; and
c) isolating the recombinant virus produced in step b).

In a further embodiment, a West-Nile virus neutralisation assay is provided. Accordingly, the assay comprises the steps of:
a) contacting VERO cells with West-Nile virus and an antibody;
b) culturing said VERO cells under conditions which allow for West-Nile virus replication; and
c) measuring reduction of West-Nile virus replication foci on said VERO cells.

EXAMPLES

The present invention will be more readily understood by referring to the following examples. These examples are illustrative of the wide range of applicability of the present invention and are not intended to limit its scope. Modifications and variations can be made therein without departing from the spirit and scope of the invention. Although any methods and materials similar or equivalent to those described herein can be used in the practice for testing of the present invention, the preferred methods and materials are described.

Example 1

Construction of Measles Viruses (MV) Expressing WNV and DEN1 Antigens

In order to test their capacity as vaccine candidates against WNV infection, recombinant Schwarz measles viruses (MV) expressing these WNV and DEN-1 antigens were constructed. The different genes were introduced in an additional transcription unit in the Schwarz MV cDNA that the inventors previously cloned (pTM-MVSchw) (European Patent Application No 02291551.6 filed on Jun. 20, 2002). After rescue of the different recombinant Schwarz measles viruses expressing the WNV and DEN-1 genes, their capacity to protect mice from a lethal WNV intraperitoneal challenge, and monkeys from Dengue virus infection will be tested.
MV Vector Mass vaccination with live attenuated vaccines has reduced the incidence of measles and its complications dramatically since it was introduced in the 60's. By now, the vaccine has been given to billions of people and is safe and efficacious. It induces a very efficient, life-long CD4, CD8 and humoral immunity after a single injection of 104 TCID50. Moreover, it is easy to produce, cheap, and the means to deliver it worldwide already exist. The safety of this vaccine is due to several factors: i) The stability of the MV genome which explains that reversion to pathogenicity has never been observed. ii) The impossibility for the MV genome to integrate in host chromosomes since viral replication is exclusively cytoplasmic. iii) The production of the vaccine on safe primary chick embryo fibroblastic cells. Thus, live attenuated MV could provide a safe and efficient pediatric vaccination vector.

MV belongs to the genus *Morbillivirus* in the family Paramyxoviridae. The Edmonston MV was isolated in 1954 (32), serially passaged on primary human kidney and amnion cells, then adapted to chick embryo fibroblasts (CEF) to produce Edmonston A and B seeds (see (7, 8) for review). Edmonston B was licensed in 1963 as the first MV vaccine. Further passages of Edmonston A and B on CEF produced the more attenuated Schwarz and Moraten viruses (33) whose sequences have recently been shown to be identical (34, 35). Being "reactogenic," Edmonston B vaccine was abandoned in 1975 and replaced by the Schwarz/Moraten vaccine. This is now the most commonly used measles vaccine (7, 8).

In a previous work, the inventors constructed an infectious cDNA from a batch of commercial Schwarz vaccine, a widely used MV vaccine (European Patent Application No 02291551.6 filed on Jun. 20, 2002). The extremities of the cDNA were engineered in order to maximize virus yield during rescue. A previously described helper cell-based rescue system was adapted by co-cultivating transfected cells on primary chick embryo fibroblasts, the cells used to produce the Schwarz vaccine. After two passages the sequence of the rescued virus was identical to that of the cDNA and of the published Schwarz sequence. Two additional transcription units (ATU) were introduced in the cDNA for cloning foreign genetic material. The immunogenicity of rescued virus was studied in mice transgenic for the CD46 MV receptor and in macaques. Antibody titers in animals inoculated with low doses of the rescued virus were identical to those obtained with commercial Schwarz MV vaccine. In contrast, the immunogenicity of a previously described Edmonston strain-derived MV clone was much lower. This new molecular clone allows producing MV vaccine without having to rely on seed stocks. The ATUs, allow producing recombinant vaccines based on an approved, efficient and worldwide used vaccine strain.

Example 2

Construction of Schwarz MV-WNV Recombinant Plasmids

1) Secreted Glycoprotein E from WNV

The WNV env gene encoding the secreted form of the protein was generated by RT-PCR amplification of viral RNA purified from viral particles (WNV IS-98-ST1 strain). The specific sequence was amplified using PfuTurbo DNA polymerase (Stratagene) and specific primers that contain unique sites for subsequent cloning in pTM-MVSchw vector: MV-WNEnv5 5'-TATCGTACGATGAGAGTTGT-GTTTGTCGTGCTA-3' (SEQ ID NO: 9) (BsiWI site underlined) and MV-WNEnv3 5'-ATAGCGCGCTTAGACAGCCTTCCCAACTGA-3' (SEQ ID NO: 10) (BssHII site underlined). A start and a stop codon were added at both ends of the gene. The whole sequence generated is 1380 nucleotides long (see FIG. 1), including the start and the stop codons and respects the "rule of six", stipulating that the nucleotides number of MV genome must be divisible by 6 (28, 29). The Env protein thus generated contains its signal peptide in N-term (18 aa) and no transmembrane region. Thus, It represents amino acids 275-732 in WNV polyprotein and has the sequence shown in FIG. 2.

2) preM Plus E Glycoproteins from WNV

The WNV gene encoding the preM plus E glycoproteins was generated by PCR amplification of plasmid pVL prM-E.55.1 (clone CNCM 1-2732 deposited on Oct. 15, 2001). This expression plasmid encodes the pre-M and E proteins of WNV (IS-98-ST1 strain). The sequence was amplified using PfuTurbo DNA polymerase (Stratagene) and specific primers that contain unique sites for subsequent cloning in pTM-MVSchw vector: MV-WNpreME5 5'-TATCGTACGATG-CAAAAGAAAAGAGGAGGAAAG-3' (SEQ ID NO: 11) (BsiWI site underlined) and MV-WNpreME3 5'-AT-AGCGCGCTTAAGCGTGCACGTTCACGGAG-3' (SEQ ID NO: 12) (BssHII site underlined). A start and a stop codon were added at both ends of the gene. The whole sequence generated is 2076 nucleotides long (see FIG. 3), including the start and the stop codons and respects the MV "rule of six". In this construct, the C-terminus part of the C protein serves as a prM translocation signal. Both preM and E viral glycoproteins are transmembrane glycoproteins type I. It is presumed that WNV env preME expressing MV will produce and release multimeric forms of preM-E heterodimers exhibiting high immunogenic potential. The construct represents amino acids 302-789 in WNV polyprotein and has the sequence shown in FIG. 4.

3) NS1 Protein from WNV

The WNV NS1 gene was generated by RT-PCR amplification of viral RNA purified from viral particles (WNV IS-98-ST1 strain). The specific sequence was amplified using PfuTurbo DNA polymerase (Stratagene) and specific primers: MV-WNNS15 5'-TATCGTACGATGAGGTCCAT-AGCTCTCACG-3' (SEQ ID NO: 13) (BsiWI site underlined) and MV-WNNS13 5'-ATAGCGCGCTCATTAGGTCTTTTCATCATGTCTC-3' (SEQ ID NO: 14) (BssHII site underlined). A start codon was added at the 5' end and two stop codons at the 3' end of the sequence. The whole sequence is 1110 nucleotides long (see FIG. 5), including the start and the two stop codons, thus respecting the "rule of six". The NS1 protein generated contains its signal peptide sequence in N-term (23 aa). It represents amino acids 769-1136 in WNV polyprotein and has the sequence shown in FIG. 6.

4) preM-E Protein from Dengue Type 1 Virus

The Dengue virus gene encoding the preM plus E glycoproteins was generated by PCR amplification of plasmid pVL pIND/[prM+E] (clone 2) (COURAGEOT, M.-P., et al. 2000, A-glucosidase inhibitors reduce dengue virus production by affecting the initial steps of virion morphogenesis in the endoplasmic reticulum. Journal of Virology 74: 564-572). This plasmid encodes the pre-M and E glycoproteins of DEN-1 virus (strain FGA/89). The sequence was amplified using PfuTurbo DNA polymerase (Stratagene) and specific primers that contain unique sites for subsequent cloning in pTM-MVSchw vector: MV-DEN1preME5 5'-TATCGTACGAT-GAACAGGAGGAAAAGATCCGTG-3' (SEQ ID NO: 15) (BsiWI site underlined) and MV-DEN1preME3 5'-AT-AGCGCGCTTAAACCATGACTCCTAGGTACAG-3' (SEQ ID NO: 16) (BssHII site underlined). A start and a stop codon were added at both ends of the gene. The whole sequence generated is 2040 nucleotides long (see FIG. 7), including the start and the stop codons and respects the MV "rule of six". In this construct, the C-terminus part of the C protein serves as a preM translocation signal. Both preM and E viral glycoproteins are transmembrane glycoproteins type I. It is presumed that DEN-1 env expressing MV will produce and release multimeric forms of preM-E heterodimers exhibiting high immunogenic potential. The construct represents amino acids 95-773 in DEN-1 polyprotein and has the sequence shown in FIG. 8.

The same immunogens can be prepared by the same way from DEN-2, DEN-3 and DEN-4 serotypes.

5) Insertion into MV Schwarz Vector

Figure 9:
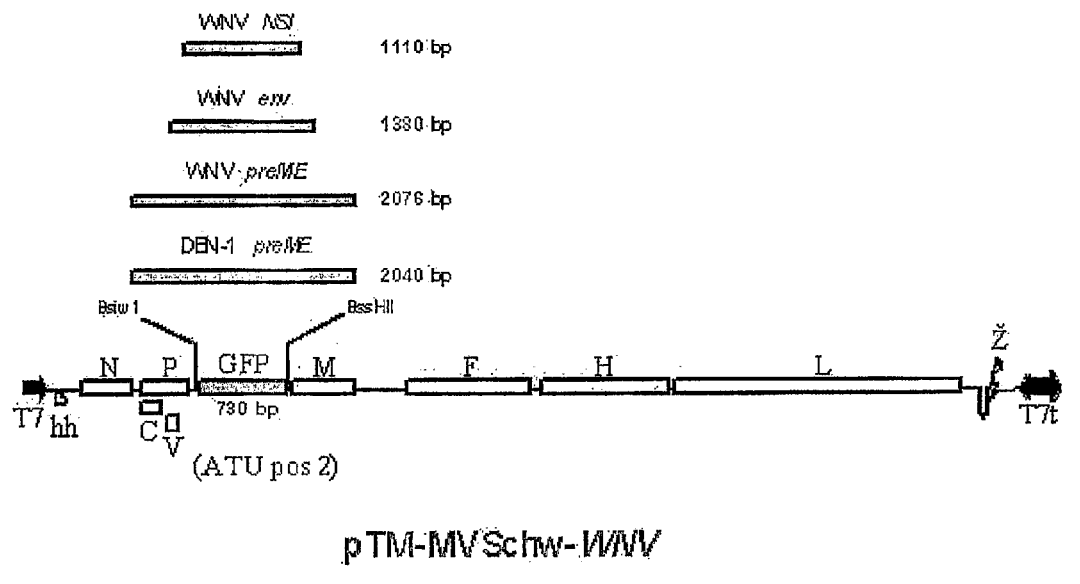

The different WNV and DEN-1 nucleotidic sequences were cloned in pCR2.1-TOPO plasmid (Invitrogen) and sequenced to check that no mutations were introduced. After BsiWI/BssHII digestion of the pCR2.1-TOPO plasmids, the DNA fragments were cloned in the pTM-MVSchw vector in ATU position 2 giving plasmids: pTM-MVSchw-EnvWNV, pTM-MVSchw-preMEwnv, pTM-MVSchw-NS1WNV and pTM-MVSchw-preMEDEN-1 according to FIG. 9.

Example 3

Recovery of Recombinant MVSchw-EnvWNV, MVSchw-preMEwnv and MVSchw-NS1WNV Viruses To recover recombinant Schwarz viruses from the plasmids, we used the helper-cell-based rescue system described by Radecke et al. (11) and modified by Parks et al. (30). Human helper cells stably expressing T7 RNA polymerase and measles N and P proteins (293-3-46 cells, a kind gift from MA Billeter) were transfected using the calcium phosphate procedure with pTM-MVSchw-EnvWNV, pTM-MVSchw-preMEwnv or pTM-MVSchw-NS1WNV plasmids (5 µg) and a plasmid expressing the MV polymerase L gene (pEMC-La, 20 ng, a kind gift from MA Billeter). After overnight incubation at 37° C., the transfection medium was replaced by fresh medium and a heat shock was applied (43° C. for two hours) (30). After two days of incubation at 37° C., transfected cells were transferred on a CEF cells layer and incubated at 32° C. in order to avoid any adaptation of the Schwarz vaccine that was originally selected on CEF cells and is currently grown on these cells for safety considerations. Infectious virus was easily recovered between 3 and 7 days following cocultivation. Syncytia appeared occasionally in CEF, but not systematically. The recombinant viruses were also rescued by the same technique after cocultivation of transfected 293-3-46 helper cells at 37° C. with primate Vero cells (african green monkey kidney). In this case, syncytia appeared systematically in all transfections after 2 days of coculture. In order to increase the yield of rescue and because these recombinant viruses will be used in mice experiments, Vero cells were used as target cells in place of the usual chick embryo fibroblasts (CEF) (European Patent Application No 02291551.6 files on Jun. 20, 2002). Recombinant viruses were passaged two times on Vero cells. The inventors have previously shown that two passages of the Schwarz virus on Vero cells did not change its immunogenic capacities in macaques (European Patent Application No 02291551.6 files on Jun. 20, 2002).

The recombinant viruses were prepared as described above and the expression of the transgene in infected cells was checked by immunofluorescence. To detect WNV Envelope glycoproteins expression, immune sera from mice resistant to WNV infection were used (International Patent Application WO 02/081741). To detect NS1 protein expression, the inventors used anti-NS1 Monoclonal antibodies (International Patent Application No WO 00/75665).

Example 4

Vaccination Against West-Nile Virus

West Nile disease has recently emerged as an important mosquito-borne *flavivirus* infection with numerous fatal cases of human encephalitis, thus urging to develop a safe and efficient vaccine. Measles virus (MV) vaccine, a live-attenuated RNA virus, is one of the safest and most effective human vaccine developed so far. The Schwarz vaccine strain of MV can be used as a vector to immunize against heterologous viral, thereby offering a novel and attractive vaccination strategy against West Nile virus (WNV). We evaluated the efficacy of a Schwarz measles vaccine-derived vector expressing the secreted form of the WNV envelope E glycoprotein in a mouse model. Vaccination induced high titers of specific anti-WNV neutralizing antibodies and protection from a lethal WNV challenge. Passive administration with antisera from immunized mice also provided protection, even after challenge with high doses of WNV. Example 4 is the first report that a live-attenuated recombinant measles virus provides efficient protective immunity against an heterologous viral disease. The induction of protective immunity shows that live attenuated-MV expressing the secreted form of the E glycoprotein is an effective vaccine against West Nile disease.

Materials and Methods

Cells and Virus.

Vero-NK (African green monkey kidney) cells were maintained in DMEM Glutamax (Invitrogen) supplemented with 5% heat-inactivated fetal bovine serum (FBS). Helper 293-3-46 cells used for viral rescue (11) (a kind gift from M. Billeter, Zurich University) were grown in DMEM/10% FBS and supplemented with 1.2 mg of G 418 per ml. WNV strain IS-98-ST1 (GenBank accession number AF 481864) was propagated in mosquito *Aedes pseudoscutellaris* AP61 cell monolayers (13). Purification on sucrose gradients, and virus titration on AP61 cells by focus immunodetection assay (FIA) were performed as previously described (13, 27).

Mouse Antisera to WNV.

Anti-WNV hyperimmune mouse ascitic fluid (HMAF) was obtained by repeated immunization of adult mice with WNV strain IS-98-ST1 followed by the inoculation of sarcoma 180. Mouse polyclonal anti-WNV antibodies were obtained by immunization of adult BALB/c-MBT congenic mice with $10^3$ FFU of IS-98-ST1 as described previously (13). The WNV-immune serum was collected one month after priming.

Construction of pTM-MVSchw-sE$_{WNV}$ Plasmid.

The plasmid pTM-MVSchw that contains an infectious MV cDNA corresponding to the anti-genome of the widely used Schwarz/Moraten MV vaccine strain has been reported elsewhere (10). Additional transcription units were introduced into the viral genome to turn it into a vector expressing foreign proteins. To construct pTM-MVSchw-sE$_{WNV}$, genomic RNA of WNV was extracted from highly purified IS-98-ST1 virions and reverse transcribed using Titan One-Step RT-PCR kit (Roche Molecular Biochemicals) according to the manufacturer's instructions. An RT-PCR fragment encoding the internal E translocation signal (prM-151 to prM-166) followed by the ectodomain and the stem region of the E protein (E-1 to E-441) was generated using the 5' primer MV-WNEnv5 5'-TAT CGTACGATGAGAGTTGTGTTTGTCGTGCTA-3' (SEQ ID NO: 9) containing a BsiWI restriction site (underlined) and the 3' primer MV-WNEnv3 5'-ATA GCGCGCTTAGACAGCCTTCCCAACTGA-3' (SEQ ID NO: 10) containing a BssHII restriction site (underlined). A start and a stop codon were added at both ends of the gene. The sequence respects the <<rule of six>>, stipulating that the nucleotides number of MV genome must be multiple of 6 (28, 29). The PCR product was directly inserted into pCR2.1-TOPO plasmid (TOPO TA cloning kit, Invitrogen) according to the manufacturer's instructions to give TOPO-sE$_{WNV}$. A 1.4-kb fragment containing truncated E protein with translocation signal sequence was excised from TOPO-sE$_{WNV}$ using BsiWI and BssHII and then inserted into BsiWI/BssHII-digested pTM-MVSchw-ATU2 which contains the additional transcription unit (ATU) between the P and M genes of Schwarz MV genome (10, 11). The resulting plasmid was designated pTM-MVSchw-sE$_{WNV}$ (named pTM-MVSchw-EnvWVN in the previous Examples). All constructs were verified by automated sequencing.

Rescue of Recombinant MVSchw-sE$_{WNV}$ Virus from the Cloned cDNA.

Rescue of recombinant Schwarz MV from the plasmid pTM-MVSchw-sE$_{WNV}$ was performed using the helper-cell-based rescue system described by Radecke et al. (11) and modified by Parks et al. (30). Briefly, human helper cells stably expressing T7 RNA polymerase and measles N and P proteins (293-3-46 cells, a kind gift from MA Billeter, Zurich University) were transfected with 5 µg pTM-MVSchw-sE$_{WNV}$ and 0.02 µg pEMC-La expressing the MV polymerase L gene (a kind gift from MA Billeter) using the calcium phosphate procedure. After overnight incubation at 37° C., a heat shock was applied for 2 h at 43° C. After two days of incubation at 37° C., transfected cells were transferred onto a Vero cell monolayer. Vero cells were used as target cells in place of the usual chick embryo fibroblasts (CEF) in order to increase the yield of rescued virus. The inventors have previously shown that two passages of the Schwarz virus on Vero cells did not change its immunogenicity in primates (10). Syncytia that appeared after 2-3 days of coculture were transferred to 35 mm wells of Vero cells, then expanded in 75- and then 150-cm² flasks in DMEM/5% FBS. When syncytia reached 80-90% confluence (usually 36-48 h post-infection), the cells were scraped in a small volume of OptiMEM (Invitrogen) and frozen and thawed once. After low-speed centrifugation to pellet cellular debris, the supernatant, which contained virus, was stored at −80° C. The titers of MVSchw-sE$_{WNV}$ was determined by an endpoint limit dilution assay on Vero cells. The 50% tissue culture infectious doses (TCID$_{50}$) were calculated using the Kärber method.

Radioimmunoprecipitation Assay.

Vero cells were starved for 1 h with DMEM without methionine and cysteine (ICN Biomedicals) and labeled 3 h with 250 µCi/ml Tran$^{35}$S-label (ICN Biomedicals). Cells were lysed with RIPA buffer (20 mM TrisCl, pH 8.0, 150 mM NaCl, 10 mM EDTA, 0.1% SDS, 0.5% deoxycholate, 1% Triton X-100) supplemented with a cocktail of protease inhibitors. RIP assay was performed as previously described (31). Samples were analyzed by SDS-15% PAGE under reducing conditions.

Mice Experiments.

CD46-IFNAR mice were produced as previously described (10). Adult BALB/c mice were purchased from Janvier Laboratories (Le Genest St Isle, France). Mice were housed under specific pathogen-free conditions at the Pasteur Institute. Five to 6-week-old CD46-IFNAR mice were i.p. inoculated with $10^4$ or $10^6$ TCID$_{50}$ of MV. Acute WNV challenge was performed by i.p. inoculation of neurovirulent WNV strain IS-98-ST1 (i.p.LD$_{50}$=10) in Dulbecco's modified phosphate saline buffer (DPBS) supplemented with 0.2% bovine serum albumin (BSA) pH 7.5 (Sigma Chemical Co.). The animals were monitored daily for signs of morbidity and mortality. All experiments are approved and conducted in accordance with the guidelines of the Office Laboratory Animal Care at Pasteur Institute.

Anti-WN Vaccination Test with Antigenic Boost.

Adult CD46$^{+/-}$ IFN-α/βR$^{-/-}$ mice were vaccinated over a four week period with the MV-WN sE virus at a dose of $10^4$ DCIP50 (which is a dose recommended for humans) and an antigenic boost was provided by purified WNV pseudo-particles that were secreted by MEF/3T3.Tet-Off/WN prME#h2 cells.

Humoral Response.

To evaluate the specific antibody response in serum, mice were bled via the periorbital route at different time after inoculation. Detection of anti-MV antibodies was performed by ELISA (Trinity Biotech, USA) as previously described (10). An anti-mouse antibody-HRP conjugate (Amersham) was used as the secondary antibody. The endpoint titer was calculated as the reciprocal of the last dilution giving a positive optical density value. The presence of anti-WNV antibodies was assessed by ELISA as previously described (13). Briefly, microtitration plaques were coated with 106 FFU of highly purified WNV strain IS-98-ST1 and then incubated with mouse sera dilutions. A test serum was considered positive if its optical density was twice the optical density of sera from immunized control mice.

Neutralization Assay.

Anti-WNV neutralizing antibodies were detected by a FRNT test. Sera from each mouse group were pooled and heat-inactivated at 56° C. for 30 min. Vero cells were seeded into 12-well plate ($1.5 \times 10^5$ cells/well) for 24 h. Mouse serum samples were serially diluted in MEM Glutamax/2% FBS. Dilutions (0.1 ml) were incubated at 37° C. for 2 h and under gentle agitation with an equal volume of WNV strain IS-98-ST1 containing ~100 FFU. Remaining infectivity was then assayed on Vero cell monolayer overlaid with MEM Glutamax/2% FBS containing 0.8% (W/V) carboxy methyl cellulose (BDH). After 2 days of incubation at 37° C. with 5% $CO_2$, FIA was performed with anti-WNV HMAF as previously described (27). The highest serum dilution tested that reduced the number of FFU by at least 90% ($FRNT_{90}$) was considered the end-point titer.

Passive Transfer of Immune Sera.

Pooled immune sera were transferred into 6-week-old female BALB/c mice intraperitoneally. Mice received injection of 0.1 ml of serial dilutions of pooled serum samples in DPBS/0.2% BSA one day before WNV inoculation. The challenged mice were observed for more than 3 weeks.

Discussion of the Results

Since its introduction into the United States in 1999, West Nile virus (WNV) infection has been recognized as one of the most serious mosquito-borne disease in the Western Hemisphere, causing severe neurological disease (meningoencephalitis and poliomyelitis-like syndrome) in humans. (3). Within the last 4 years, WNV had spread through North America, Central America and the Caribbean (1, 2). It is presumed that it will reach South America in the coming years. Since 2002, the US outbreaks were characterized by an apparent increase in human disease severity with 13,000 cases and 500 deaths. Although mosquito-borne transmission of WNV predominates, WNV is also transmitted by blood transfusion, organ donations and transplacentaly to the fetus (3). Prevention of West Nile encephalitis is a new public health priority and it is imperative that a vaccine be developed (3, 4, 5). No vaccine has been approved for human use so far.

Because WNV can be transmitted across species, there is an urgent need to develop preventive strategies for humans. A rational approach should be to confer a long-term immunity in large groups of individuals, and to boost this immunity in case of WNV outbreaks. Measles virus (MV) vaccine can now be used as a vector to immunize against heterologous viral diseases, thereby offering a novel and attractive vaccination strategy against WNV. We have recently tested this vector against HIV infection (6). MV vaccine, a live-attenuated RNA virus, is one of the safest and most effective human vaccine developed so far. It induces a very efficient, life-long immunity after a single or two injections (7, 8). The MV genome is very stable and reversion of vaccine strains to pathogenicity has never been observed. The Schwarz MV strain is used in two widely used measles vaccines, Attenuavax (Merck and Co. Inc., West Point, USA) and Rouvax (Aventis Pasteur, Marcy I'Etoile, France), and in the combined measles, mumps, and rubella vaccine (MMR) (9). We have recently generated an infectious cDNA for this strain (10) and introduced additional transcription units (ATU) into it for cloning foreign genes, based on the work of Radecke et al. (11). The vaccine rescued from the molecular clone was as immunogenic as the parental vaccine in primates and mice susceptible to MV infection. Thus, this approved and widely used MV vaccine can be used as a vector to immunize individuals simultaneously against measles and other infectious diseases.

Figure 10:
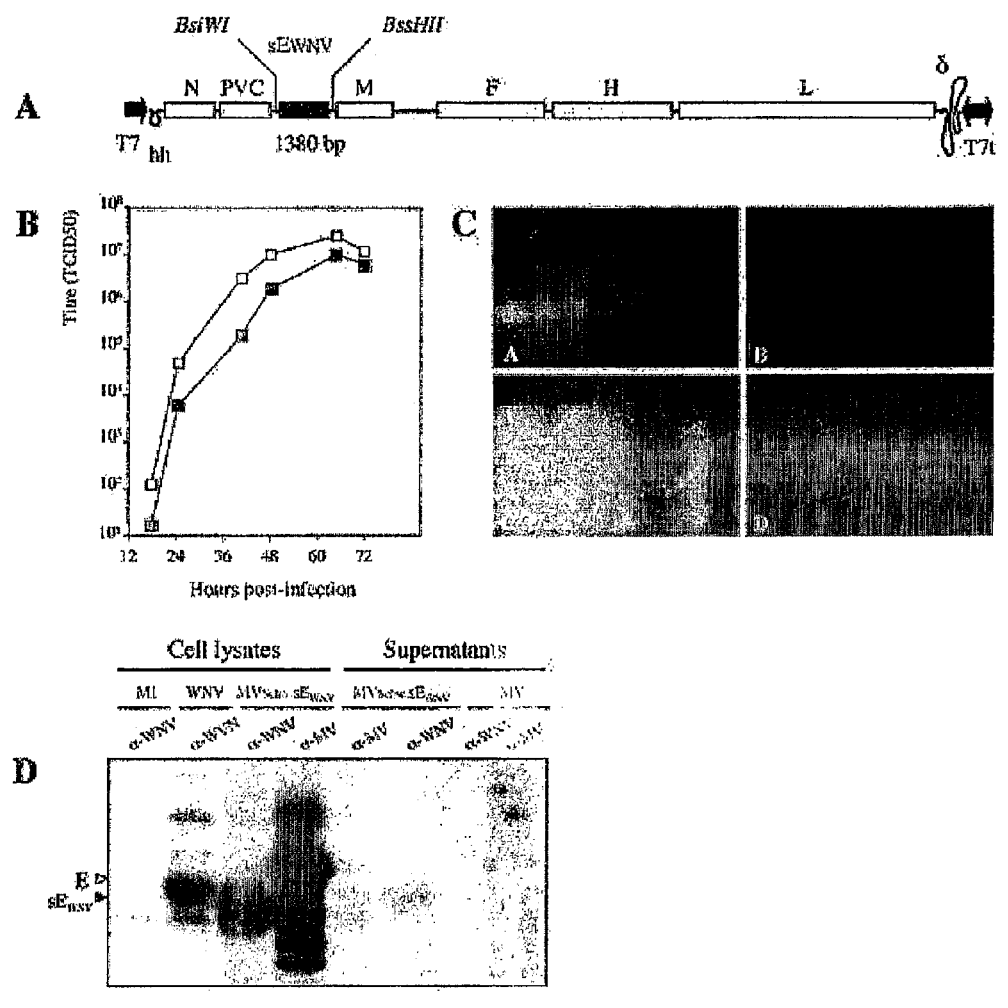

WNV is a single-stranded RNA virus of the Flaviviridae family, genus *flavivirus*, within the Japanese encephalitis antigenic complex (2, 3). The virion is composed of three structural proteins, designated C (core protein), M (membrane protein) and E (envelope protein). Protein E, which is exposed on the surface of the virion, is responsible for virus attachment and virus-specific membrane fusion. Because the E glycoprotein can potentially serve as a major protective immunogen for a WNV vaccine (12), the inventors introduced the WNV cDNA encoding the carboxyl-terminally truncated E glycoprotein lacking the transmembrane-anchoring region (residues E-1 to E-441, designated $sE_{WNV}$ hereinafter) of IS-98-ST1 strain (13) into the infectious cDNA for the Schwarz MV vaccine (10) (FIG. 10A). WNV strain IS-98-ST1 has the same neuropathologic properties than the new variant designated Isr98/NY99 that has been responsible for the recent WNV outbreaks in North America and Middle East (13). The WNV sequence was introduced in an ATU located between the phosphoprotein (P) and matrix (M) genes in the MV genome. The recombinant $MVSchw-sE_{WNV}$ virus was produced after transfection of the corresponding plasmid into human helper cells allowing the rescue of negative-stranded RNA paramyxoviruses (11), then propagation in Vero cell cultures. The growth of $MV_{Schw}$-$sE_{WNV}$ in Vero cells was only slightly delayed as compared to that of standard Schwarz MV ($MV_{Schw}$) (FIG. 10B). After 60 h of infection, the yield of $MV_{Schw}$-$sE_{WNV}$ was comparable to that of $MV_{Schw}$. The expression of $sE_{WNV}$ in $MV_{Schw}$-$sE_{WNV}$-infected Vero cells was demonstrated by immunofluorescence and radioimmunoprecipitation (RIP) assays (FIG. 10C, D). At 40 h post-infection, the cell surface of $MV_{Schw}$-$sE_{WNV}$-induced syncitia was clearly visualized by anti-WNV immune serum, indicating that $sE_{WNV}$ is transported along the compartments of the secretory pathway (FIG. 10C). RIP analysis revealed that anti-WNV antibodies recognized $sE_{WNV}$ that migrated faster than authentic E glycoprotein (FIG. 10D). Interestingly, $sE_{WNV}$ was detected in the supernatants of $MV_{Schw}$-$sE_{WNV}$-infected Vero cells at 40 h post-infection (FIG. 10D, panel Supernatants/$MV_{Schw}$-$sE_{WNV}$, lane α-WNV). Thus, $MV_{Schw}$-$sE_{WNV}$ expresses a recombinant E glycoprotein which is secreted efficiently. Immunoblots confirmed that $sE_{WNV}$ accumulated in the culture medium of $MV_{Schw}$-$sE_{WNV}$-infected Vero cells (data not shown).

Figure 11:
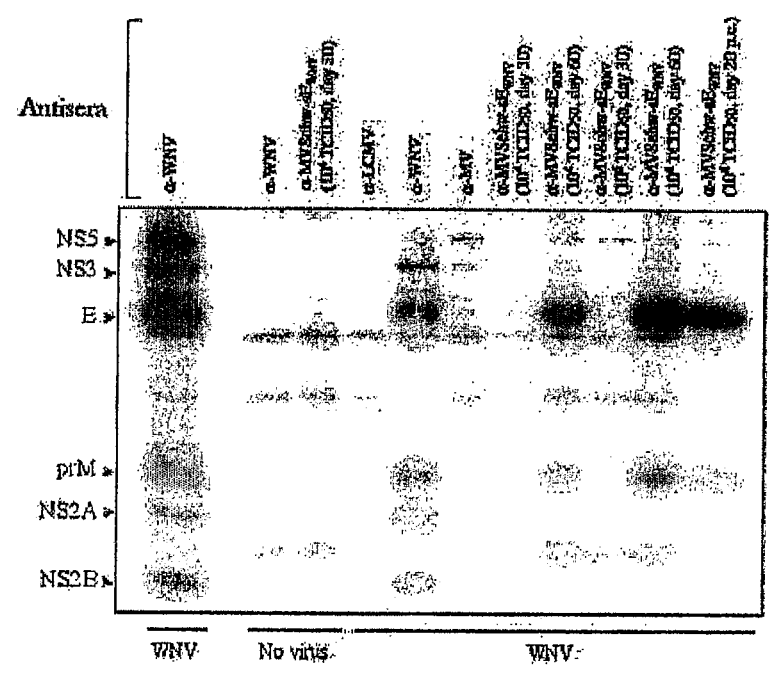

Genetically modified mice expressing the human CD46 MV receptor and lacking the interferon α/β receptor (6, 14) ($CD46^{+/-}$ IFN-α/β $R^{-/-}$, abbreviated CD46-IFNAR) that are susceptible to MV (14) were used to assess the immune response induced by $MV_{Schw}$-$sE_{WNV}$. These mice deficient in IFN-α/β response raise cellular and humoral immune responses similar to those of competent mice (6, 10, 15, 16). Two groups of six CD46-IFNAR mice were inoculated intraperitoneally (i.p.) with either $10^4$ or $10^6$ tissue culture infective doses ($TCID_{50}$) of $MV_{Schw}$-$sE_{WNV}$. Each group was boosted using the same dose 1 month after the first immunization. As a control, CD46-IFNAR mice were immunized with $10^6$ $TCID_{50}$ of "empty" $MV_{Schw}$. One month after the first immunization, specific anti-MV antibodies were detected in immune sera from mice inoculated with either $MV_{Schw}$ or $MV_{Schw}$-$sE_{WNV}$ (Table 1). Mice that received either dose of $MV_{Schw}$-$sE_{WNV}$ displayed specific anti-WNV antibodies at a dilution of 1:3,000. One month after boosting, the titers of anti-WNV antibodies had reached 1:30,000 to 1:200,000 (Table 1) and were highly reactive with the WNV E glycoprotein (FIG. 11). No anti-WNV antibodies were detected in the sera of any control mice (Table 1 and FIG. 11). These results show that one injection of $MV_{Schw}$-$sE_{WNV}$ induces anti-WNV antibodies, and that boosting one month after priming increases their titers 10 to 60 times.

Anti-WNV neutralizing activity was measured in $MV_{Schw}$-$sE_{WNV}$-immune sera using a focus reduction test ($FRNT_{90}$) (Table 1). As a positive control, the WNV-immune serum from immunized BALB/c-MBT congenic mice (13) gave a $FRNT_{90}$ titer of 50. The immune sera from CD46-IFNAR mice inoculated with "empty" $MV_{Schw}$ had not detectable neutralizing activity. Immunized CD46-IFNAR mice which received $10^4$ or $10^6$ TCID$_{50}$ of MV$_{Schw}$-sE$_{WNV}$ raised neutralizing antibodies with similar FRNT$_{90}$ titers, and boosting increased their titers from 10 to 200-300. These data show that mice twice inoculated with the recombinant live-attenuated MV encoding the secreted form of the IS-98-ST1 E glycoprotein had high levels of anti-WNV antibody with neutralizing activity, regardless of the injected dose.

Because antibody-mediated immunity may be critical to protect against WNV infection (17, 18), the inventors examined if the passive transfer of sera from MV$_{Schw}$-sE$_{WNV}$-immunized mice can protect adult BALB/c mice from WNV infection (Table 2). Groups of six 6-week-old BALB/c mice received i.p. various amounts of pooled immune sera from MV$_{Schw}$-sE$_{WNV}$-immunized CD46-IFNAR mice collected one month after priming or boosting. One day later, the mice were challenged with 10 times the i.p. 50% lethal dose (LD$_{50}$) of WNV strain IS-98-ST1 (13, 19). As a positive control, BALB/c mice that received as little as 2 µl of the WNV-immune serum were protected from the challenge (Table 2). In contrast, all mice that received 2 µl of the non-immune mouse serum or serum from "empty" MV$_{Schw}$-immunized mice died within 11-12 days. Protective passive immunity was observed in all BALB/c mice following transfer of 2 µl of pooled sera from CD46-IFNAR mice immunized once with $10^6$ TCID$_{50}$ of MVSchw-sE$_{WNV}$. As little as 1 µl of this antisera induced 66% protection. Passive transfer of sera collected one month after a single immunization with $10^4$ TCID$_{50}$ induced a survival rate of 50%. Remarkably, the administration of 1 µl of MV$_{Schw}$-sE$_{WNV}$-immune sera collected 1 month after boosting induced 100% protection. These results indicate that a single injection of $10^6$ TCID$_{50}$ or two injections of $10^4$ TCID$_{50}$ of MV$_{Schw}$-sE$_{WNV}$ elicited protective humoral response. Because the amount of *flavivirus* inoculated during mosquito feeding is probably in the order of $10^2$ to $10^4$ infectious virus particles (1), we assessed the capacity of MV$_{Schw}$-sE$_{WN}$-immune sera to protect against a range of $10^2$ to $10^5$ focus forming units (FFU) of WNV strain IS-98-ST1. Groups of six BALB/c mice were passively immunized with 2 µl of pooled immune sera collected from CD46-IFNAR mice twice inoculated with $10^4$ TCID$_{50}$ of MV$_{Schw}$-sE$_{WNV}$ (Table 2). Survival rates of 85-100% were observed in mice that received the MV$_{Schw}$-sE$_{WNV}$-immune serum, regardless the lethal doses of IS-98-ST1 (10 to 10,000 i.p. LD$_{50}$). These data are consistent with the finding that humoral response plays a critical role in protection against WNV infection.

Mice which are completely unresponsive to IFN-α/β are highly susceptible to encephalitic *flaviviruses* (19, 20). Indeed, the inventors previously showed that WNV infection of CD46-IFNAR mice was lethal within 3 days instead of 11 days in competent mice (19). To assess whether the immunity induced by MVSchw-sE$_{WNV}$ could protect these compromised animals from WNV infection, three CD46-IFNAR mice from the group that had received two injections of MV$_{Schw}$-sE$_{WNV}$ ($10^6$ TCID$_{50}$), were i.p. inoculated with 100 FFU of IS-98-ST1 one month after the boost. Mice inoculated with "empty" MV$_{Schw}$ were used as controls. The mice that had received MV$_{Schw}$-sE$_{WNV}$ survived the WNV challenge while control mice died within 3 days. MV$_{Schw}$-sE$_{WNV}$-immunized mice were bled 3 weeks after challenge. The FRNT$_{90}$ antibody response (titer ~100) was comparable to the pre-challenge response. Notably, post-challenge immune sera did not react with WNV nonstructural proteins such as NS3 and NS5 as shown by RIP assay (FIG. 11, panel MV$_{Schw}$-sE$_{WNV}$, lane $10^6$ TCID$_{50}$, day 20, p.c.), suggesting that no viral replication occurred after challenge with WNV. These data show that immunizing with MV$_{Schw}$-sE$_{WNV}$ prevented WNV infection in highly susceptible animals.

The present Example shows for the first time that a live-attenuated measles vector derived from the Schwarz MV vaccine can induce a protective immunity against an heterologous lethal pathogen. These data constitute also the proof of concept that a live-attenuated Schwarz measles vaccine engineered to express the secreted form of the WNV E glycoprotein can be used as a vaccine to prevent West Nile disease in humans. The MV vaccine vector offers several advantages (over other existing viral vectors. The Schwarz MV vaccine has been used on billions of people since the sixties and shown to be safe and efficacious. It is easily produced on a large scale in most countries and can be distributed at low cost. The MV genome is very stable and reversion to pathogenicity has never been observed (8). Moreover, MV replicates exclusively in the cytoplasm, ruling out the possibility of integration in host DNA. The MV vector has been shown to express a variety of genes, or combinations of genes, of large size over more than twelve passages (6, 16, 21, 22, 23, 24). This stability is likely due to the fact that there is little constraint on genome size for pleomorphic viruses with a helical nucleocapsid. Unlike chimeric viral vectors, the recombinant MV vector is an authentic MV expressing an additional gene. This greatly reduces the risk, of changing the tropism and the pathogenicity of the original vaccine. It reduces also the risk of recombination.

The recombinant MV-WNV vaccine according to a preferred embodiment of the present invention is a promising live-attenuated vector to mass immunize children and adolescents against both measles and West Nile diseases. Although the existence of an anti-MV immunity in nearly the entire adult human population appears to restrict its use to infants, an already worthy goal, recent studies demonstrated that revaccinating already immunized children results in a boost of anti-MV antibodies (25, 26). These and other studies (Ann Arvin) demonstrated that the presence of passive MV pre-immunity (maternal antibodies) does not circumvent the replication of attenuated MV after a second injection. This opens the possibility of using the live-attenuated MV-derived vector to immunize adults. Indeed, the inventors reported that a MV-HIV recombinant virus induced anti-HIV neutralizing antibodies in mice and macaques even in the presence of pre-existing anti-MV immunity (6). Because of cross-species transmission, it is feared that WNV becomes a recurrent zoonosis with repeated seasonal outbreaks in humans. The inventors propose that MVSchw-sE$_{WNV}$ could be used to induce long-term memory immunity in large groups of children and adults, and to boost this immunity in case of West Nile disease outbreak.

BIBLIOGRAPHY

1. D. W. C. Beasley, et al., Virology 309, 190-5 (2003).
2. M. A. Brinton, Annu. Rev. Microbial 56, 371-402 (2002).
3. L. R. Petersen, A. A. Marfin, D. J. Gubler, JAMA 290, 524-28 (2003).
4. T. Monath, Ann. N.Y. Acad. Sci 951, 1-12 (2001).
5. T. P. Monath, J. Arroyo, F. Guirakhoo, Curr. Drug Targets Infect Disord 1, 37-50 (2001).
6. C. Lorin, et al., Journal of Virology 78, in press (2004).
7. D. Griffin, in Field's Virology, 4th Edition D. Knipe, P. Howley, Eds. (Lippincott—Raven Publishers, Philadelphia, 2001), vol. 2, pp. 1401-1441.
8. M. Hilleman, Vaccine 20, 651-665 (2002).
9. E. Buynak, R. Weibel, W. J. JE, J. Stokes Jr, M. Hilleman, J. Am. Med. Assoc. 207, 2259-2262 (1969).

10. C. Combredet, et al., Journal of Virology 77, 11546-11554 (2003).
11. F. Radecke, et al., Embo J 14, 5773-84. (1995).
12. T. Wang, et al., J. Immunol. 167, 5273-5277 (2001).
13. T. Mashimo, et al., Proc. Natl. Acad. Sci. USA 99, 11311-11316 (2002).
14. B. Mrkic, et al., J Virol 72, 7420-7 (1998).
15. U. Muller, et al., Science 264, 1918-21. (1994).
16. M. Singh, R. Cattaneo, M. A. Billeter, J Virol 73, 4823-8. (1999).
17. M. S. Diamond, B. Shrestha, A. Marri, D. Mahan, M. Engle, J. Virol. 77, 2578-2586 (2003).
18. M. Haley, A. S. Retter, D. Fowler, J. Gea-Banacloche, N. P. O'Grady, Clin. Infect. Dis. 37, 88-90 (2003).
19. M. Lucas, et al., Immun. Cell Biol. 81, 230-236 (2003).
20. M. Lobigs, A. Müllbacher, Y. Wang, M. Pavy, E. Lee, J. Gen. Virol. 84, 567-572 (2003).
21. F. Radecke, M. Billeter, Reviews in Medical Virology 7, 49-63 (1997).
22. P. Spielhofer, et al., J. Viral. 72, 2150-2159 (1998).
23. M. Singh, M. Billeter, J. Gen. Virol. 80, 101-6 (1999).
24. Z. Wang, et al., Vaccine 19, 2329-2336 (2001).
25. A. Dilraj, et al., Lancet 355, 798-803 (2000).
26. A. Dilraj, et al., Pediatr. Infect. Dis. J. 19, 1211-3. (2000).
27. P. Desprès, M.-P. Frenkiel, V. Deubel, Virology 196, 209-219 (1993).
28. P. Calain, L. Roux, J Virol 67, 4822-30 (1993).
29. H. Schneider, K. Kaelin, M. A. Billeter, Virology 227, 314-22. (1997).
30. C. L. Parks, R. A. Lerch, P. Walpita, M. S. Sidhu, S. A. Udem, J Virol 73, 3560-6 (1999).
31. P. Desprès, J. W. Griffin, D. E. Griffin, J. Virol. 69, 7345-7348 (1995).
32. Enders, J. F. & Peebles, T. C. (1954) Proc. Soc. Exp. Biol. Med. 86, 277-286.
33. Schwarz, A. (1962) Am. J. Dis. Child. 103, 216-219.
34. Parks, C. L., Lerch, R. A., Walpita, P., Wang, H. P., Sidhu, M. S. & Udem, S. A. (2001) J Virol 75, 910-20.
35. Parks, C. L., Lerch, R. A., Walpita, P., Wang, H. P., Sidhu, M. S. & Udem, S. A. (2001) J Virol 75, 921-33.

TABLE 1

Antibody response of CD46-IFNAR mice to intraperitoneal inoculation of $MV_{Schw}$-$sE_{WNV}$

| Immunizing virus | MV-specific Ab titer[4] | WN-specific Ab titer[4] | WN-specific FRNT$_{90}$[5] |
|---|---|---|---|
| WNV[1] ($10^3$ FFU) | NT | 10,000 | 50 |
| $MV_{Schw}$[2] ($10^6$ TCID$_{50}$) | 30,000 | <10 | <10 |
| $MV_{Schw}$-$sE_{WNV}$[2] ($10^4$ TCID$_{50}$) | 15,000 | 3,000 | 10 |
| $MV_{Schw}$-$sE_{WNV}$[2] ($10^6$ TCID$_{50}$) | 25,000 | 3,000 | 10 |
| 2 × $MV_{Schw}$-$sE_{WNV}$[3] ($10^4$ TCID$_{50}$) | 90,000 | 30,000 | 200 |
| 2 × $MV_{Schw}$-$sE_{WNV}$[3] ($10^6$ TCID$_{50}$) | 140,000 | 200,000 | 300 |

[1]BALB/c-MBT congenic mice were i.p. inoculated with WNV strain IS-98-ST1.
[2]Virus was given i.p. to CD46-IFNAR mice.
[3]Virus was given i.p. twice at 1 month of interval.
[4]Determined by ELISA on pooled heat-inactivated sera.
[5]The highest serum dilution that reduced the number of FFU of WNV by at least 90%.
NT: not tested

TABLE 2

Protective ability of the $MV_{Schw}$-$sE_{WNV}$-immune serum

| Material used for immunization | Volume of sera transferred[1] (□l) | WNV[2] (FFU) | Protection (no. surviving/ no. tested) | M.D.O.D[3] (day ± S.D.) |
|---|---|---|---|---|
| Controls | | | | |
| DPBS | 10 | 100 | 0/6 | 11.5 ± 1.5 |
| WNV[4] | 10 | 100 | 6/6 | — |
|  | 2 | 100 | 5/6 | 20 |
| MVSchw[5] | 2 | 100 | 0/6 | 12.0 ± 1.5 |
| MVSchw-$sE_{WNV}$[6] | | | | |
| $10^6$ TCID50 (day 30) | 2 | 100 | 6/6 | — |
|  | 1 | 100 | 4/6 | 11.0 ± 1.5 |
| $10^4$ TCID50 (day 30) | 10 | 100 | 3/6 | 10.5 ± 2.0 |
| $10^4$ TCID50 (day 60) | 1 | 100 | 6/6 | — |
|  | 2 | 100 | 5/6 | 11 |
|  | 2 | 1,000 | 6/6 | — |
|  | 2 | 10,000 | 5/6 | 10 |
|  | 2 | 100,000 | 5/6 | 11 |

[1]BALB/c mice received 0.1 ml of DPBS containing the indicated amount of pooled sera.
[2]Mice were challenged with WNV strain IS-98-ST1 one day after passive transfer.
[3]Mean day of death ± standard deviation.
[4]Immune sera from resistant BALB/c-MBT congenic mice (13) inoculated with $10^3$ FFU of IS-98-ST1 WNV.
[5]Immune sera from CD46-IFNAR mice collected 30 days after inoculation of MVSchw ($10^6$ TCID$_{50}$).
[6]Immune sera from CD46-IFNAR mice were collected 30 days after 1 injection or 60 days after 2 injections of MVSchw-$sE_{WNV}$.

What is claimed is:

1. A recombinant measles virus, comprising a polynucleotide coding for a polypeptide which is the West-Nile virus (WNV) secreted envelope glycoprotein (sE) of SEQ ID NO: 5;
   wherein the recombinant measles virus is a live attenuated measles virus; and
   wherein the recombinant measles virus induces an immune response that limits growth and spread of an infectious WNV when administered to an animal.

2. The recombinant measles virus of claim 1, wherein the polynucleotide comprises the polynucleotide sequence of SEQ ID NO: 1.

3. A recombinant measles virus genome that encodes the recombinant measles virus of claim 1.

4. The recombinant measles virus of claim 1, which is a recombinant Schwarz measles virus strain.

5. A pharmaceutical composition comprising:
   a) the recombinant measles virus of claim 1; and
   b) a pharmaceutically acceptable vehicle or carrier.

6. A method for limiting growth and spread of an infectious WNV in an animal, comprising administering an effective amount of the pharmaceutical composition of claim 5 to the animal.

7. An isolated host cell comprising the recombinant measles virus of claim 1.

8. A method of producing a recombinant measles virus, the method comprising:
   a) providing the isolated host cell of claim 7;
   b) placing the isolated host cell in conditions permitting the replication of the recombinant virus; and
   c) isolating the recombinant virus produced in b).

9. A method for limiting growth and spread of an infectious WNV in an animal, comprising administering an effective amount of the recombinant measles virus of claim 1 to the animal.

10. A recombinant measles virus, comprising a polynucleotide coding for a polypeptide
    sequence selected from the group consisting of SEQ ID NO:6, SEQ ID NO: 5, and SEQ ID NO:8;
    wherein the recombinant measles virus is a live attenuated measles virus; and
    wherein the recombinant measles virus induces an immune response against the encoded polypeptide when administered to an animal.

11. The recombinant measles virus of claim 10, wherein the polypeptide comprises the sequence of SEQ ID NO: 5.

12. The recombinant measles virus of claim 10, wherein the polypeptide comprises the sequence of SEQ ID NO:6.

13. The recombinant measles virus of claim 10, wherein the polypeptide comprises the sequence of or SEQ ID NO:8.

14. The recombinant measles virus of claim 10, which is a recombinant Schwarz measles virus strain.

* * * * *

SEQUENCE LISTING

<160> NUMBER OF SEQ ID NOS: 16

<210> SEQ ID NO 1
<211> LENGTH: 1380
<212> TYPE: DNA
<213> ORGANISM: West Nile virus

<400> SEQUENCE: 1

```
atgagagttg tgtttgtcgt gctattgctt ttggtggccc cagcttacag cttcaactgc    60
cttggaatga gcaacagaga cttcttggaa ggagtgtctg gagcaacatg ggtggatttg   120
```

-continued

```
gttctcgaag gcgacagctg cgtgactatc atgtctaagg acaagcctac catcgatgtg      180
aagatgatga atatggaggc ggtcaacctg gcagaggtcc gcagttattg ctatttggct      240
accgtcagcg atctctccac caaagctgcg tgcccgacca tgggagaagc tcacaatgac      300
aaacgtgctg acccagcttt tgtgtgcaga caaggagtgg tggacagggg ctggggcaac      360
ggctgcggat tatttggcaa aggaagcatt gacacatgcg ccaaatttgc ctgctctacc      420
aaggcaatag gaagaaccat cttgaaagag aatatcaagt acgaagtggc cattttttgtc     480 catggaccaa ctactgtgga gtcgcacgga aactactcca cacaggttgg agccactcag      540
gcagggagat tcagcatcac tcctgcggcg ccttcataca cactaaagct ggagaatat       600 ggagaggtga cagtggactg tgaaccacgg tcagggattg acaccaatgc atactacgtg      660
atgactgttg aacaaagac gttcttggtc catcgtgagt ggttcatgga cctcaacctc       720
ccttggagca gtgctggaag tactgtgtgg aggaacagag agacgttaat ggagtttgag      780
gaaccacacg ccacgaagca gtctgtgata gcattgggct cacaagaggg agctctgcat      840
caagctttgg ctggagccat tcctgtgaa ttttcaagca cactgtcaa gttgacgtcg        900 ggtcatttga agtgtagagt gaagatgaa aaattgcagt tgaagggaac aacctatggc      960
gtctgttcaa aggcttttca gtttcttggg actcccgcag acacaggtca cggcactgtg     1020
gtgttggaat tgcagtacac tggcacggat ggaccttgca agttcctat ctcgtcagtg      1080 gcttcattga acgacctaac gccagtgggc agattggtca ctgtcaaccc ttttgtttca     1140
gtggccacgg ccaacgctaa ggtcctgatt gaattggaac cacccttggg agactcatac    1200
atagtggtgg gcagaggaga acaacagatc aatcaccatt ggcacaagtc tggaagcagc   1260
attggcaaag cctttacaac cacccctcaaa ggagcgcaga gactagccgc tctaggagac   1320
acagcttggg actttggatc agttggaggg gtgttcacct cagttgggaa ggctgtctaa   1380
```

<210> SEQ ID NO 2
<211> LENGTH: 2076
<212> TYPE: DNA
<213> ORGANISM: West Nile virus

<400> SEQUENCE: 2

```
atgcaaaaga aaagaggagg aaagaccgga attgcagtca tgattggcct gatcgccagc       60
gtaggagcag ttacctctc taacttccaa gggaaggtga tgatgacggt aaatgctact      120
gacgtcacag atgtcatcac gattccaaca gctgctggaa agaacctatg cattgtcaga    180
gcaatggatg tgggatacat gtgcgatgat actatcactt atgaatgccc agtgctgtcg    240
gctggtaatg atccagaaga catcgactgt tggtgcacaa agtcagcagt ctacgtcagg    300
tatggaagat gcaccaagac acgccactca gacgcagtc ggaggtcact gacagtgcag     360
acacacggag aaagcactct agcgaacaag aagggggctt ggatggacag caccaaggcc    420
acaaggtatt tggtaaaaac agaatcatgg atcttgagga accctggata tgccctggtg    480
gcagccgtca ttgttggat gcttgggagc aacaccatgc agagagttgt gtttgtcgtg    540
ctattgcttt tggtggcccc agcttacagc ttcaactgcc ttggaatgag caacagagac    600
ttcttggaag gagtgtctgg agcaacatgg gtggatttgg ttctcgaagg cgacagctgc   660
gtgactatca tgtctaagga caagcctacc atcgatgtga agatgatgaa tatggaggcg   720
gtcaacctgg cagaggtccg cagttattgc tatttggcta ccgtcagcga tctctccacc   780
aaagctgcgt gcccgaccat gggagaagct cacaatgaca acgtgctga cccagctttt    840 gtgtgcagac aaggagtggt ggacaggggc tggggcaacg gctgcggatt atttggcaaa    900
```

```
ggaagcattg acacatgcgc caaatttgcc tgctctacca aggcaatagg aagaaccatc     960
ttgaaagaga atatcaagta cgaagtggcc attttttgtcc atggaccaac tactgtggag   1020
tcgcacggaa actactccac acaggttgga gccactcagg cagggagatt cagcatcact   1080
cctgcggcgc cttcatacac actaaagctt ggagaatatg gagaggtgac agtggactgt   1140
gaaccacggt cagggattga caccaatgca tactacgtga tgactgttgg aacaaagacg   1200
ttcttggtcc atcgtgagtg gttcatggac ctcaacctcc cttggagcag tgctggaagt   1260
actgtgtgga ggaacagaga gacgttaatg gagtttgagg aaccacacgc cacgaagcag   1320
tctgtgatag cattgggctc acaagaggga gctctgcatc aagctttggc tggagccatt   1380
cctgtggaat tttcaagcaa cactgtcaag ttgacgtcgg tcatttgaa gtgtagagtg     1440
aagatggaaa aattgcagtt gaagggaaca acctatggcg tctgttcaaa ggctttcaag   1500
tttcttggga ctcccgcaga cacaggtcac ggcactgtgg tgttggaatt gcagtacact   1560
ggcacggatg gaccttgcaa agttcctatc tcgtcagtgg cttcattgaa cgacctaacg   1620
ccagtgggca gattggtcac tgtcaaccct tttgtttcag tggccacggc caacgctaag   1680
gtcctgattg aattggaacc acccttggga gactcataca tagtggtggg cagaggagaa   1740
caacagatca atcaccattg gcacaagtct ggaagcagca ttggcaaagc ctttacaacc   1800
accctcaaag gagcgcagag actagccgct ctaggagaca cagcttggga ctttggatca   1860
gttggagggg tgttcacctc agttgggaag gctgtccatc aagtgttcgg aggagcattc   1920
cgctcactgt tcggaggcat gtcctggata acgcaaggat tgctggggc tctcctgttg   1980
tggatgggca tcaatgctcg tgataggtcc atagctctca cgtttctcgc agttggagga   2040
gttctgctct cctctccgt gaacgtgcac gcttaa                              2076
```

```
<210> SEQ ID NO 3
<211> LENGTH: 1110
<212> TYPE: DNA
<213> ORGANISM: West Nile virus

<400> SEQUENCE: 3
atgaggtcca tagctctcac gtttctcgca gttggaggag ttctgctctt cctctccgtg     60
aacgtgcacg ctgacactgg tgtgccata gacatcagcc ggcaagagct gagatgtgga   120
agtggagtgt tcatacacaa tgatgtggag gcttggatgg accggtacaa gtattaccct   180
gaaacgccac aaggcctagc caagatcatt cagaaagctc ataaggaagg agtgtgcggt   240
ctacgatcag tttccagact ggagcatcaa atgtgggaag cagtgaagga cgagctgaac   300
actcttttga aggagaatgg tgtggacctt agtgtcgtgg ttgagaaaca ggagggaatg   360
tacaagtcag cacctaaacg cctcaccgcc accacgaaa aattggaaat tggctggaag   420
gcctggggaa agagtatttt atttgcacca gaactcgcca acaacacctt tgtggttgat   480
ggtccggaga ccaaggaatg tccgactcag atcgcgctt ggaatagctt agaagtggag   540
gattttggat tggtctcac cagcactcgg atgttcctga aggtcagaga gagcaacaca   600
actgaatgtg actcgaagat cattggaacg gctgtcaaga acaacttggc gatccacagt   660
gacctgtcct attggattga aagcaggctc aatgatacgt ggaagcttga agggcagtt   720
ctgggtgaag tcaaatcatg tacgtggcct gagacgcata ccttgtgggg cgatggaatc   780
cttgagagtg acttgataat accagtcaca ctggcgggac cacgaagcaa tcacaatcgg   840
agacctgggt acaagacaca aaaccagggc ccatgggacg aaggccgggt agagattgac   900
```

```
ttcgattact gcccaggaac tacggtcacc ctgagtgaga gctgcggaca ccgtggacct    960
gccactcgca ccaccacaga gagcggaaag ttgataacag attggtgctg caggagctgc   1020
accttaccac cactgcgcta ccaaactgac agcggctgtt ggtatggtat ggagatcaga   1080
ccacagagac atgatgaaaa gacctaatga                                    1110

<210> SEQ ID NO 4
<211> LENGTH: 2040
<212> TYPE: DNA
<213> ORGANISM: Dengue virus type 1

<400> SEQUENCE: 4
atgaacagga ggaaaagatc cgtgaccatg ctcctcatgc tgctgcccac agtcctggct    60
ttccatttga ccacgcgagg gggagagcca cacatgatag ttagtaagca ggaaagagga   120
aagtcactct tgttcaagac ctctgcaggt gtcaatatgt gcactctcat tgcgatggat   180
ttgggagagt tatgtgagga cacaatgact acaaatgccc ccggatcact gaggcggaa    240 ccagatgacg ttgactgctg gtgcaatgcc acagacacat gggtgaccta tgggacgtgt   300
tctcaaaccg gtaacaccg acgagacaaa cgttccgtgg cactggcccc acacgtggga   360
cttggtctag aaacaagaac cgaaacatgg atgtcctctg aaggcgcctg gaaacaaata   420
caaaaagtgg agacttgggc tttgagacac ccaggattca cggtgatagc tcttttttta   480
gcacatgcca taggaacatc catcactcag aaagggatca ttttcattct gctgatgctg   540
gtaacaccat caatggccat gcgatgcgtg ggaataggca acagagactt cgttgaagga   600
ctgtcaggag caacgtgggt ggacgtggta ttggagcatg gaagctgcgt caccaccatg   660
gcaaaaaata accaacatt ggacattgaa ctcttgaaga cggaggtcac gaaccctgcc   720
gtcttgcgca aattgtgcat tgaagctaaa atatcaaaca ccaccaccga ttcaagatgt   780
ccaacacaag gagaggctac actggtggaa gaacaagacg cgaactttgt gtgtcgacga   840
acggttgtgg acagaggctg gggcaatggc tgcggactat ttggaaaagg aagcctactg   900
acgtgtgcta agttcaagtg tgtgacaaaa ctggaaggaa agatagttca atatgaaaac   960
ttaaaatatt cagtgatagt cactgtccac acaggggacc agcaccaggt gggaaacgag  1020
actacagaac atggaacaat tgcaaccata cacctcaagc tcctacgtc ggaaatacag  1080 ttgacagact acggaacct tacactggac tgctcacccca gaacagggct ggactttaat  1140
gaggtggtgc tattgacaat gaaagaaaaa tcatggcttg tccacaaaca atggtttcta  1200
gacttaccac tgccttggac ttcgggggct caacatccc aagagacttg aacagacaa   1260 gatttgctgg tcacattcaa gacagctcat gcaaagaagc aggaagtagt cgtactggga  1320
tcacaggaag gagcaatgca cactgcgttg accggggcga cagaaatcca gacgtcagga  1380
acgacaacaa tctttgcagg acacctgaaa tgcagattaa aaatggataa actgactta  1440 aaagggatgt catatgtgat gtgcacaggc tcatttaagc tagagaagga agtggctgag  1500
acccagcatg gaactgtcct agtgcaggtt aaatacgaag aacagatgc gccatgcaag  1560 atccccttt cgacccaaga tgagaaagga gtgacccaga tgggagatt gataacagcc  1620 aatcccatag ttactgacaa agaaaaacca atcaacattg agacagaacc accttttggt  1680
gagagctaca tcatagtagg ggcaggtgaa aaagctttga aactaagctg gttcaagaaa  1740
ggaagcagca tagggaaaat gttcgaagca atcgcccgag agcacgaag gatggctatc  1800 ctgggagaca ccgcatggga cttcggctct ataggaggg tgtttacgtc tgtgggaaaa  1860
ttggtacacc aggttttgg aaccgcatac gggtcctgt tcagcggcgt tcttggacc   1920
```

```
atgaaaatag gaataggat cttgctgaca tggttgggat taaattcaag gagcgcgtcg   1980
ctttcgatga cgtgcattgc agttggcatg gttacactgt acctaggagt catggtttaa   2040
```

<210> SEQ ID NO 5
<211> LENGTH: 459
<212> TYPE: PRT
<213> ORGANISM: West Nile virus

<400> SEQUENCE: 5

```
Met Arg Val Val Phe Val Val Leu Leu Leu Val Ala Pro Ala Tyr
1               5                   10                  15

Ser Phe Asn Cys Leu Gly Met Ser Asn Arg Asp Phe Leu Glu Gly Val
            20                  25                  30

Ser Gly Ala Thr Trp Val Asp Leu Val Leu Glu Gly Asp Ser Cys Val
        35                  40                  45

Thr Ile Met Ser Lys Asp Lys Pro Thr Ile Asp Val Lys Met Met Asn
    50                  55                  60

Met Glu Ala Val Asn Leu Ala Glu Val Arg Ser Tyr Cys Tyr Leu Ala
65                  70                  75                  80

Thr Val Ser Asp Leu Ser Thr Lys Ala Ala Cys Pro Thr Met Gly Glu
                85                  90                  95

Ala His Asn Asp Lys Arg Ala Asp Pro Ala Phe Val Cys Arg Gln Gly
            100                 105                 110

Val Val Asp Arg Gly Trp Gly Asn Gly Cys Gly Leu Phe Gly Lys Gly
        115                 120                 125

Ser Ile Asp Thr Cys Ala Lys Phe Ala Cys Ser Thr Lys Ala Ile Gly
    130                 135                 140

Arg Thr Ile Leu Lys Glu Asn Ile Lys Tyr Glu Val Ala Ile Phe Val
145                 150                 155                 160

His Gly Pro Thr Thr Val Glu Ser His Gly Asn Tyr Ser Thr Gln Val
                165                 170                 175

Gly Ala Thr Gln Ala Gly Arg Phe Ser Ile Thr Pro Ala Ala Pro Ser
            180                 185                 190

Tyr Thr Leu Lys Leu Gly Glu Tyr Gly Glu Val Thr Val Asp Cys Glu
        195                 200                 205

Pro Arg Ser Gly Ile Asp Thr Asn Ala Tyr Tyr Val Met Thr Val Gly
    210                 215                 220

Thr Lys Thr Phe Leu Val His Arg Glu Trp Phe Met Asp Leu Asn Leu
225                 230                 235                 240

Pro Trp Ser Ser Ala Gly Ser Thr Val Trp Arg Asn Arg Glu Thr Leu
                245                 250                 255

Met Glu Phe Glu Glu Pro His Ala Thr Lys Gln Ser Val Ile Ala Leu
            260                 265                 270

Gly Ser Gln Glu Gly Ala Leu His Gln Ala Leu Ala Gly Ala Ile Pro
        275                 280                 285

Val Glu Phe Ser Ser Asn Thr Val Lys Leu Thr Ser Gly His Leu Lys
    290                 295                 300

Cys Arg Val Lys Met Glu Lys Leu Gln Leu Lys Gly Thr Thr Tyr Gly
305                 310                 315                 320

Val Cys Ser Lys Ala Phe Lys Phe Leu Gly Thr Pro Ala Asp Thr Gly
                325                 330                 335

His Gly Thr Val Val Leu Glu Leu Gln Tyr Thr Gly Thr Asp Gly Pro
            340                 345                 350
```

```
Cys Lys Val Pro Ile Ser Ser Val Ala Ser Leu Asn Asp Leu Thr Pro
            355                 360                 365

Val Gly Arg Leu Val Thr Val Asn Pro Phe Val Ser Val Ala Thr Ala
    370                 375                 380

Asn Ala Lys Val Leu Ile Glu Leu Glu Pro Pro Phe Gly Asp Ser Tyr
385                 390                 395                 400

Ile Val Val Gly Arg Gly Glu Gln Gln Ile Asn His His Trp His Lys
                405                 410                 415

Ser Gly Ser Ser Ile Gly Lys Ala Phe Thr Thr Thr Leu Lys Gly Ala
            420                 425                 430

Gln Arg Leu Ala Ala Leu Gly Asp Thr Ala Trp Asp Phe Gly Ser Val
        435                 440                 445

Gly Gly Val Phe Thr Ser Val Gly Lys Ala Val
    450                 455

<210> SEQ ID NO 6
<211> LENGTH: 691
<212> TYPE: PRT
<213> ORGANISM: West Nile virus

<400> SEQUENCE: 6

Met Gln Lys Lys Arg Gly Gly Lys Thr Gly Ile Ala Val Met Ile Gly
1               5                   10                  15

Leu Ile Ala Ser Val Gly Ala Val Thr Leu Ser Asn Phe Gln Gly Lys
            20                  25                  30

Val Met Met Thr Val Asn Ala Thr Asp Val Thr Asp Val Ile Thr Ile
                35                  40                  45

Pro Thr Ala Ala Gly Lys Asn Leu Cys Ile Val Arg Ala Met Asp Val
    50                  55                  60

Gly Tyr Met Cys Asp Asp Thr Ile Thr Tyr Glu Cys Pro Val Leu Ser
65                  70                  75                  80

Ala Gly Asn Asp Pro Glu Asp Ile Asp Cys Trp Cys Thr Lys Ser Ala
                85                  90                  95

Val Tyr Val Arg Tyr Gly Arg Cys Thr Lys Thr Arg His Ser Arg Arg
            100                 105                 110

Ser Arg Arg Ser Leu Thr Val Gln Thr His Gly Glu Ser Thr Leu Ala
        115                 120                 125

Asn Lys Lys Gly Ala Trp Met Asp Ser Thr Lys Ala Thr Arg Tyr Leu
    130                 135                 140

Val Lys Thr Glu Ser Trp Ile Leu Arg Asn Pro Gly Tyr Ala Leu Val
145                 150                 155                 160

Ala Ala Val Ile Gly Trp Met Leu Gly Ser Asn Thr Met Gln Arg Val
                165                 170                 175

Val Phe Val Val Leu Leu Leu Leu Val Ala Pro Ala Tyr Ser Phe Asn
            180                 185                 190

Cys Leu Gly Met Ser Asn Arg Asp Phe Leu Glu Gly Val Ser Gly Ala
        195                 200                 205

Thr Trp Val Asp Leu Val Leu Glu Gly Asp Ser Cys Val Thr Ile Met
    210                 215                 220

Ser Lys Asp Lys Pro Thr Ile Asp Val Lys Met Met Asn Met Glu Ala
225                 230                 235                 240

Val Asn Leu Ala Glu Val Arg Ser Tyr Cys Tyr Leu Ala Thr Val Ser
                245                 250                 255

Asp Leu Ser Thr Lys Ala Ala Cys Pro Thr Met Gly Glu Ala His Asn
            260                 265                 270
```

```
Asp Lys Arg Ala Asp Pro Ala Phe Val Cys Arg Gln Gly Val Val Asp
        275                 280                 285

Arg Gly Trp Gly Asn Gly Cys Gly Leu Phe Gly Lys Gly Ser Ile Asp
        290                 295                 300

Thr Cys Ala Lys Phe Ala Cys Ser Thr Lys Ala Ile Gly Arg Thr Ile
305                 310                 315                 320

Leu Lys Glu Asn Ile Lys Tyr Glu Val Ala Ile Phe Val His Gly Pro
        325                 330                 335

Thr Thr Val Glu Ser His Gly Asn Tyr Ser Thr Gln Val Gly Ala Thr
                340                 345                 350

Gln Ala Gly Arg Phe Ser Ile Thr Pro Ala Ala Pro Ser Tyr Thr Leu
        355                 360                 365

Lys Leu Gly Glu Tyr Gly Glu Val Thr Val Asp Cys Glu Pro Arg Ser
        370                 375                 380

Gly Ile Asp Thr Asn Ala Tyr Tyr Val Met Thr Val Gly Thr Lys Thr
385                 390                 395                 400

Phe Leu Val His Arg Glu Trp Phe Met Asp Leu Asn Leu Pro Trp Ser
                405                 410                 415

Ser Ala Gly Ser Thr Val Trp Arg Asn Arg Glu Thr Leu Met Glu Phe
        420                 425                 430

Glu Glu Pro His Ala Thr Lys Gln Ser Val Ile Ala Leu Gly Ser Gln
        435                 440                 445

Glu Gly Ala Leu His Gln Ala Leu Ala Gly Ala Ile Pro Val Glu Phe
        450                 455                 460

Ser Ser Asn Thr Val Lys Leu Thr Ser Gly His Leu Lys Cys Arg Val
465                 470                 475                 480

Lys Met Glu Lys Leu Gln Leu Lys Gly Thr Thr Tyr Gly Val Cys Ser
                485                 490                 495

Lys Ala Phe Lys Phe Leu Gly Thr Pro Ala Asp Thr Gly His Gly Thr
        500                 505                 510

Val Val Leu Glu Leu Gln Tyr Thr Gly Thr Asp Gly Pro Cys Lys Val
        515                 520                 525

Pro Ile Ser Ser Val Ala Ser Leu Asn Asp Leu Thr Pro Val Gly Arg
        530                 535                 540

Leu Val Thr Val Asn Pro Phe Val Ser Val Ala Thr Ala Asn Ala Lys
545                 550                 555                 560

Val Leu Ile Glu Leu Glu Pro Pro Phe Gly Asp Ser Tyr Ile Val Val
                565                 570                 575

Gly Arg Gly Glu Gln Gln Ile Asn His His Trp His Lys Ser Gly Ser
        580                 585                 590

Ser Ile Gly Lys Ala Phe Thr Thr Thr Leu Lys Gly Ala Gln Arg Leu
        595                 600                 605

Ala Ala Leu Gly Asp Thr Ala Trp Asp Phe Gly Ser Val Gly Gly Val
        610                 615                 620

Phe Thr Ser Val Gly Lys Ala Val His Gln Val Phe Gly Gly Ala Phe
625                 630                 635                 640

Arg Ser Leu Phe Gly Gly Met Ser Trp Ile Thr Gln Gly Leu Leu Gly
                645                 650                 655

Ala Leu Leu Leu Trp Met Gly Ile Asn Ala Arg Asp Arg Ser Ile Ala
        660                 665                 670

Leu Thr Phe Leu Ala Val Gly Gly Val Leu Leu Phe Leu Ser Val Asn
        675                 680                 685
```

```
Val His Ala
    690

<210> SEQ ID NO 7
<211> LENGTH: 368
<212> TYPE: PRT
<213> ORGANISM: West Nile virus

<400> SEQUENCE: 7

Met Arg Ser Ile Ala Leu Thr Phe Leu Ala Val Gly Gly Val Leu Leu
1               5                   10                  15

Phe Leu Ser Val Asn Val His Ala Asp Thr Gly Cys Ala Ile Asp Ile
            20                  25                  30

Ser Arg Gln Glu Leu Arg Cys Gly Ser Gly Val Phe Ile His Asn Asp
        35                  40                  45

Val Glu Ala Trp Met Asp Arg Tyr Lys Tyr Pro Glu Thr Pro Gln
    50                  55                  60

Gly Leu Ala Lys Ile Ile Gln Lys Ala His Lys Glu Gly Val Cys Gly
65                  70                  75                  80

Leu Arg Ser Val Ser Arg Leu Glu His Gln Met Trp Glu Ala Val Lys
                85                  90                  95

Asp Glu Leu Asn Thr Leu Leu Lys Glu Asn Gly Val Asp Leu Ser Val
            100                 105                 110

Val Val Glu Lys Gln Glu Gly Met Tyr Lys Ser Ala Pro Lys Arg Leu
        115                 120                 125

Thr Ala Thr Thr Glu Lys Leu Glu Ile Gly Trp Lys Ala Trp Gly Lys
    130                 135                 140

Ser Ile Leu Phe Ala Pro Glu Leu Ala Asn Asn Thr Phe Val Val Asp
145                 150                 155                 160

Gly Pro Glu Thr Lys Glu Cys Pro Thr Gln Asn Arg Ala Trp Asn Ser
                165                 170                 175

Leu Glu Val Glu Asp Phe Gly Phe Gly Leu Thr Ser Thr Arg Met Phe
            180                 185                 190

Leu Lys Val Arg Glu Ser Asn Thr Thr Glu Cys Asp Ser Lys Ile Ile
        195                 200                 205

Gly Thr Ala Val Lys Asn Asn Leu Ala Ile His Ser Asp Leu Ser Tyr
    210                 215                 220

Trp Ile Glu Ser Arg Leu Asn Asp Thr Trp Lys Leu Glu Arg Ala Val
225                 230                 235                 240

Leu Gly Glu Val Lys Ser Cys Thr Trp Pro Glu Thr His Thr Leu Trp
                245                 250                 255

Gly Asp Gly Ile Leu Glu Ser Asp Leu Ile Ile Pro Val Thr Leu Ala
            260                 265                 270

Gly Pro Arg Ser Asn His Asn Arg Arg Pro Gly Tyr Lys Thr Gln Asn
        275                 280                 285

Gln Gly Pro Trp Asp Glu Gly Arg Val Glu Ile Asp Phe Asp Tyr Cys
    290                 295                 300

Pro Gly Thr Thr Val Thr Leu Ser Glu Ser Cys Gly His Arg Gly Pro
305                 310                 315                 320

Ala Thr Arg Thr Thr Thr Glu Ser Gly Lys Leu Ile Thr Asp Trp Cys
                325                 330                 335

Cys Arg Ser Cys Thr Leu Pro Pro Leu Arg Tyr Gln Thr Asp Ser Gly
            340                 345                 350

Cys Trp Tyr Gly Met Glu Ile Arg Pro Gln Arg His Asp Glu Lys Thr
        355                 360                 365
```

<210> SEQ ID NO 8
<211> LENGTH: 679
<212> TYPE: PRT
<213> ORGANISM: Dengue virus type 1

<400> SEQUENCE: 8

```
Met Asn Arg Arg Lys Arg Ser Val Thr Met Leu Leu Met Leu Leu Pro
1               5                   10                  15

Thr Val Leu Ala Phe His Leu Thr Thr Arg Gly Gly Glu Pro His Met
            20                  25                  30

Ile Val Ser Lys Gln Glu Arg Gly Lys Ser Leu Leu Phe Lys Thr Ser
        35                  40                  45

Ala Gly Val Asn Met Cys Thr Leu Ile Ala Met Asp Leu Gly Glu Leu
    50                  55                  60

Cys Glu Asp Thr Met Thr Tyr Lys Cys Pro Arg Ile Thr Glu Ala Glu
65                  70                  75                  80

Pro Asp Asp Val Asp Cys Trp Cys Asn Ala Thr Asp Thr Trp Val Thr
                85                  90                  95

Tyr Gly Thr Cys Ser Gln Thr Gly Glu His Arg Arg Asp Lys Arg Ser
            100                 105                 110

Val Ala Leu Ala Pro His Val Gly Leu Gly Leu Glu Thr Arg Thr Glu
        115                 120                 125

Thr Trp Met Ser Ser Glu Gly Ala Trp Lys Gln Ile Gln Lys Val Glu
130                 135                 140

Thr Trp Ala Leu Arg His Pro Gly Phe Thr Val Ile Ala Leu Phe Leu
145                 150                 155                 160

Ala His Ala Ile Gly Thr Ser Ile Thr Gln Lys Gly Ile Ile Phe Ile
                165                 170                 175

Leu Leu Met Leu Val Thr Pro Ser Met Ala Met Arg Cys Val Gly Ile
            180                 185                 190

Gly Asn Arg Asp Phe Val Glu Gly Leu Ser Gly Ala Thr Trp Val Asp
        195                 200                 205

Val Val Leu Glu His Gly Ser Cys Val Thr Thr Met Ala Lys Asn Lys
    210                 215                 220

Pro Thr Leu Asp Ile Glu Leu Leu Lys Thr Glu Val Thr Asn Pro Ala
225                 230                 235                 240

Val Leu Arg Lys Leu Cys Ile Glu Ala Lys Ile Ser Asn Thr Thr Thr
                245                 250                 255

Asp Ser Arg Cys Pro Thr Gln Gly Glu Ala Thr Leu Val Glu Glu Gln
            260                 265                 270

Asp Ala Asn Phe Val Cys Arg Arg Thr Val Val Asp Arg Gly Trp Gly
        275                 280                 285

Asn Gly Cys Gly Leu Phe Gly Lys Gly Ser Leu Leu Thr Cys Ala Lys
    290                 295                 300

Phe Lys Cys Val Thr Lys Leu Glu Gly Lys Ile Val Gln Tyr Glu Asn
305                 310                 315                 320

Leu Lys Tyr Ser Val Ile Val Thr Val His Thr Gly Asp Gln His Gln
                325                 330                 335

Val Gly Asn Glu Thr Thr Glu His Gly Thr Ile Ala Thr Ile Thr Pro
            340                 345                 350

Gln Ala Pro Thr Ser Glu Ile Gln Leu Thr Asp Tyr Gly Thr Leu Thr
        355                 360                 365

Leu Asp Cys Ser Pro Arg Thr Gly Leu Asp Phe Asn Glu Val Val Leu
```

```
                        370             375             380
Leu Thr Met Lys Glu Lys Ser Trp Leu Val His Lys Gln Trp Phe Leu
385                     390                 395                 400

Asp Leu Pro Leu Pro Trp Thr Ser Gly Ala Ser Thr Ser Gln Glu Thr
                405                 410                 415

Trp Asn Arg Gln Asp Leu Leu Val Thr Phe Lys Thr Ala His Ala Lys
            420                 425                 430

Lys Gln Glu Val Val Leu Gly Ser Gln Glu Gly Ala Met His Thr
        435                 440                 445

Ala Leu Thr Gly Ala Thr Glu Ile Gln Thr Ser Gly Thr Thr Thr Ile
    450                 455                 460

Phe Ala Gly His Leu Lys Cys Arg Leu Lys Met Asp Lys Leu Thr Leu
465                 470                 475                 480

Lys Gly Met Ser Tyr Val Met Cys Thr Gly Ser Phe Lys Leu Glu Lys
                485                 490                 495

Glu Val Ala Glu Thr Gln His Gly Thr Val Leu Val Gln Val Lys Tyr
            500                 505                 510

Glu Gly Thr Asp Ala Pro Cys Lys Ile Pro Phe Ser Thr Gln Asp Glu
        515                 520                 525

Lys Gly Val Thr Gln Asn Gly Arg Leu Ile Thr Ala Asn Pro Ile Val
    530                 535                 540

Thr Asp Lys Glu Lys Pro Ile Asn Ile Glu Thr Glu Pro Pro Phe Gly
545                 550                 555                 560

Glu Ser Tyr Ile Ile Val Gly Ala Gly Glu Lys Ala Leu Lys Leu Ser
                565                 570                 575

Trp Phe Lys Lys Gly Ser Ser Ile Gly Lys Met Phe Glu Ala Ile Ala
            580                 585                 590

Arg Gly Ala Arg Arg Met Ala Ile Leu Gly Asp Thr Ala Trp Asp Phe
        595                 600                 605

Gly Ser Ile Gly Gly Val Phe Thr Ser Val Gly Lys Leu Val His Gln
    610                 615                 620

Val Phe Gly Thr Ala Tyr Gly Val Leu Phe Ser Gly Val Ser Trp Thr
625                 630                 635                 640

Met Lys Ile Gly Ile Gly Ile Leu Leu Thr Trp Leu Gly Leu Asn Ser
                645                 650                 655

Arg Ser Ala Ser Leu Ser Met Thr Cys Ile Ala Val Gly Met Val Thr
            660                 665                 670

Leu Tyr Leu Gly Val Met Val
        675

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tatcgtacga tgagagttgt gtttgtcgtg cta                              33

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 10
atagcgcgct tagacagcct tcccaactga                                    30

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tatcgtacga tgcaaaagaa aagaggagga aag                                 33

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atagcgcgct taagcgtgca cgttcacgga g                                   31

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tatcgtacga tgaggtccat agctctcacg                                     30

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atagcgcgct cattaggtct tttcatcatg tctc                                34

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tatcgtacga tgaacaggag gaaaagatcc gtg                                 33

```
<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atagcgcgct taaaccatga ctcctaggta cag                             33
```